US008303624B2

(12) United States Patent
Fortson

(10) Patent No.: US 8,303,624 B2
(45) Date of Patent: Nov. 6, 2012

(54) BIOABSORBABLE PLUG

(75) Inventor: Aaron M. Fortson, Fremont, CA (US)

(73) Assignee: Abbott Cardiovascular Systems, Inc., Santa Clara, CA (US)

(*) Notice: Subject to any disclaimer, the term of this patent is extended or adjusted under 35 U.S.C. 154(b) by 214 days.

(21) Appl. No.: 12/724,304

(22) Filed: Mar. 15, 2010

(65) Prior Publication Data
US 2011/0224719 A1 Sep. 15, 2011

(51) Int. Cl.
A61B 17/08 (2006.01)
A61B 17/04 (2006.01)

(52) U.S. Cl. ......................... 606/213; 606/232
(58) Field of Classification Search .................. 606/95, 606/151, 213, 232, 230; 128/831
See application file for complete search history.

(56) References Cited

U.S. PATENT DOCUMENTS

| 287,046 | A | 10/1883 | Norton |
|---|---|---|---|
| 438,400 | A | 10/1890 | Brennen |
| 1,088,393 | A | 2/1914 | Backus |
| 1,331,401 | A | 2/1920 | Summers |
| 1,596,004 | A | 8/1926 | De Bengoa |
| 1,647,958 | A | 11/1927 | Ciarlante |
| 1,880,569 | A | 10/1932 | Weis |
| 2,087,074 | A | 7/1937 | Tucker |
| 2,254,620 | A | 9/1941 | Miller |
| 2,316,297 | A | 4/1943 | Southerland et al. |
| 2,371,978 | A | 3/1945 | Perham |
| 2,453,227 | A | 11/1948 | James |
| 2,583,625 | A | 1/1952 | Bergan |
| 2,684,070 | A | 7/1954 | Kelsey |
| 2,910,067 | A | 10/1959 | White |
| 2,944,311 | A | 7/1960 | Schneckenberger |
| 2,951,482 | A | 9/1960 | Sullivan |
| 2,969,887 | A | 1/1961 | Darmstadt et al. |
| 3,015,403 | A | 1/1962 | Fuller |
| 3,113,379 | A | 12/1963 | Frank |
| 3,120,230 | A | 2/1964 | Skold |
| 3,142,878 | A | 8/1964 | Santora |
| 3,209,754 | A | 10/1965 | Brown |
| 3,482,428 | A | 12/1969 | Kapitanov et al. |

(Continued)

FOREIGN PATENT DOCUMENTS

AU 2003297432 7/2004

(Continued)

OTHER PUBLICATIONS

U.S. Appl. No. 12/897,358, filed Oct. 4, 2010, Carley.

(Continued)

Primary Examiner — Julian Woo
(74) Attorney, Agent, or Firm — Workman Nydegger; Randy Shen

(57) ABSTRACT

In one example implementation, a device for closing an opening in tissue includes a proximal end and a distal end. The device further includes a port that extends from the proximal end of the device towards the distal end of the device. In addition to extending from the proximal end of the device towards the distal end of the device, the port includes a restriction zone and a storage region. The device further includes a blocking element that is configured to move between a neutral position, located in the storage region of the port, and a blocking position, located in the restriction zone of the port. When the blocking element is in the blocking position, the blocking element cooperates with the restriction zone in the port to assist in blocking fluid flow through the port.

24 Claims, 5 Drawing Sheets

U.S. PATENT DOCUMENTS

| | | |
|---|---|---|
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,014,492 A | 3/1977 | Rothfuss |
| 4,018,228 A | 4/1977 | Goosen |
| 4,047,533 A * | 9/1977 | Perciaccante et al. ........ 606/230 |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,147,381 A | 9/1992 | Heimerl et al. |
| 5,156,609 A | 10/1992 | Nakao et al. |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,209,756 A | 5/1993 | Seedhom et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |

| | | | | | | |
|---|---|---|---|---|---|---|
| 5,290,310 A | 3/1994 | Makower et al. | | 5,643,318 A | 7/1997 | Tsukernik et al. |
| 5,292,309 A | 3/1994 | Van Tassel et al. | | 5,645,565 A | 7/1997 | Rudd et al. |
| 5,292,332 A | 3/1994 | Lee | | 5,645,566 A | 7/1997 | Brenneman et al. |
| 5,304,183 A | 4/1994 | Gourlay et al. | | 5,645,567 A | 7/1997 | Crainich |
| 5,304,184 A | 4/1994 | Hathaway et al. | | 5,649,959 A | 7/1997 | Hannam et al. |
| 5,304,204 A | 4/1994 | Bregen | | D383,539 S | 9/1997 | Croley |
| 5,306,254 A | 4/1994 | Nash et al. | | 5,674,231 A | 10/1997 | Green et al. |
| 5,309,927 A | 5/1994 | Welch | | 5,676,689 A | 10/1997 | Kensey et al. |
| 5,318,542 A | 6/1994 | Hirsch et al. | | 5,676,974 A | 10/1997 | Valdes et al. |
| 5,320,639 A | 6/1994 | Rudnick | | 5,681,334 A | 10/1997 | Evans et al. |
| 5,327,908 A | 7/1994 | Gerry | | 5,683,405 A | 11/1997 | Yacoubian et al. |
| 5,330,445 A | 7/1994 | Haaga | | 5,690,674 A | 11/1997 | Diaz |
| 5,334,216 A | 8/1994 | Vidal et al. | | 5,695,504 A | 12/1997 | Gifford, III et al. |
| 5,334,217 A | 8/1994 | Das | | 5,695,505 A | 12/1997 | Yoon |
| 5,335,680 A | 8/1994 | Moore | | 5,695,524 A | 12/1997 | Kelley et al. |
| 5,340,360 A | 8/1994 | Stefanchik | | 5,700,273 A | 12/1997 | Buelna et al. |
| 5,350,399 A | 9/1994 | Erlebacher et al. | | 5,713,899 A | 2/1998 | Marnay et al. |
| 5,352,229 A | 10/1994 | Goble et al. | | 5,716,375 A | 2/1998 | Fowler |
| 5,364,406 A | 11/1994 | Sewell, Jr. | | 5,720,755 A | 2/1998 | Dakov |
| 5,364,408 A | 11/1994 | Gordon | | 5,725,498 A | 3/1998 | Janzen et al. |
| 5,366,458 A | 11/1994 | Korthoff et al. | | 5,725,552 A | 3/1998 | Kotula et al. |
| 5,366,479 A | 11/1994 | McGarry et al. | | 5,725,554 A | 3/1998 | Simon et al. |
| 5,383,896 A | 1/1995 | Gershony et al. | | 5,728,110 A | 3/1998 | Vidal et al. |
| RE34,866 E | 2/1995 | Kensey et al. | | 5,728,114 A * | 3/1998 | Evans et al. .................. 606/213 |
| 5,392,978 A | 2/1995 | Velez et al. | | 5,728,122 A | 3/1998 | Leschinsky et al. |
| 5,395,030 A | 3/1995 | Kuramoto et al. | | 5,728,132 A | 3/1998 | Van Tassel et al. |
| 5,411,520 A | 5/1995 | Nash et al. | | 5,728,133 A | 3/1998 | Kontos |
| 5,413,571 A | 5/1995 | Katsaros et al. | | 5,732,872 A | 3/1998 | Bolduc et al. |
| 5,413,584 A | 5/1995 | Schulze | | 5,735,873 A | 4/1998 | MacLean |
| 5,416,584 A | 5/1995 | Kay | | 5,752,966 A | 5/1998 | Chang |
| 5,417,699 A | 5/1995 | Klein et al. | | 5,755,726 A | 5/1998 | Pratt et al. |
| 5,419,777 A | 5/1995 | Hofling | | 5,755,778 A | 5/1998 | Kleshinski |
| 5,423,857 A | 6/1995 | Rosenman et al. | | 5,766,217 A | 6/1998 | Christy |
| 5,425,489 A | 6/1995 | Shichman et al. | | 5,766,246 A | 6/1998 | Mulhauser et al. |
| 5,425,740 A | 6/1995 | Hutchinson, Jr. | | 5,769,870 A | 6/1998 | Salahieh et al. |
| 5,431,639 A | 7/1995 | Shaw | | 5,776,147 A | 7/1998 | Dolendo |
| 5,431,667 A | 7/1995 | Thompson et al. | | 5,779,707 A | 7/1998 | Bertholet et al. |
| 5,433,721 A | 7/1995 | Hooven et al. | | 5,782,844 A | 7/1998 | Yoon et al. |
| 5,437,631 A | 8/1995 | Janzen | | 5,782,860 A | 7/1998 | Epstein et al. |
| 5,439,479 A | 8/1995 | Shichman et al. | | 5,782,861 A | 7/1998 | Cragg et al. |
| 5,443,477 A | 8/1995 | Marin et al. | | 5,795,958 A | 8/1998 | Rao et al. |
| 5,443,481 A | 8/1995 | Lee | | 5,797,928 A | 8/1998 | Kogasaka |
| 5,445,167 A | 8/1995 | Yoon et al. | | 5,797,931 A | 8/1998 | Bito et al. |
| 5,449,359 A | 9/1995 | Groiso | | 5,797,933 A | 8/1998 | Snow et al. |
| 5,456,400 A | 10/1995 | Shichman et al. | | 5,797,958 A | 8/1998 | Yoon |
| 5,462,561 A | 10/1995 | Voda | | 5,810,776 A | 9/1998 | Bacich et al. |
| 5,464,413 A | 11/1995 | Siska, Jr. et al. | | 5,810,846 A | 9/1998 | Virnich et al. |
| 5,466,241 A | 11/1995 | Leroy et al. | | 5,810,851 A | 9/1998 | Yoon |
| 5,470,010 A | 11/1995 | Rothfuss et al. | | 5,817,113 A | 10/1998 | Gifford, III et al. |
| 5,474,557 A | 12/1995 | Mai | | 5,820,631 A | 10/1998 | Nobles |
| 5,474,569 A | 12/1995 | Zinreich et al. | | 5,827,298 A | 10/1998 | Hart et al. |
| 5,476,505 A | 12/1995 | Limon | | 5,830,125 A | 11/1998 | Scribner et al. |
| 5,478,352 A | 12/1995 | Fowler | | 5,833,698 A | 11/1998 | Hinchliffe et al. |
| 5,478,353 A | 12/1995 | Yoon | | 5,843,167 A | 12/1998 | Dwyer et al. |
| 5,478,354 A | 12/1995 | Tovey et al. | | 5,853,421 A | 12/1998 | Leschinsky et al. |
| 5,486,195 A | 1/1996 | Myers et al. | | 5,853,422 A | 12/1998 | Huebsch et al. |
| 5,497,933 A | 3/1996 | DeFonzo et al. | | 5,855,312 A | 1/1999 | Toledano |
| 5,507,744 A | 4/1996 | Tay et al. | | 5,858,082 A | 1/1999 | Cruz et al. |
| 5,507,755 A | 4/1996 | Gresl et al. | | 5,860,991 A | 1/1999 | Klein et al. |
| 5,522,840 A | 6/1996 | Krajicek | | 5,861,005 A | 1/1999 | Kontos |
| 5,527,322 A | 6/1996 | Klein et al. | | 5,868,755 A | 2/1999 | Kanner et al. |
| 5,536,251 A | 7/1996 | Evard et al. | | 5,868,763 A | 2/1999 | Spence et al. |
| 5,540,712 A | 7/1996 | Kleshinski et al. | | 5,871,474 A | 2/1999 | Hermann et al. |
| 5,540,716 A | 7/1996 | Hlavacek | | 5,871,501 A | 2/1999 | Leschinsky et al. |
| 5,544,802 A | 8/1996 | Crainich | | 5,871,525 A | 2/1999 | Edwards et al. |
| 5,547,474 A | 8/1996 | Kloeckl et al. | | 5,873,876 A | 2/1999 | Christy |
| 5,560,532 A | 10/1996 | DeFonzo et al. | | 5,879,366 A | 3/1999 | Shaw et al. |
| 5,571,120 A | 11/1996 | Yoon | | 5,891,088 A | 4/1999 | Thompson et al. |
| 5,573,784 A | 11/1996 | Badylak et al. | | 5,897,487 A | 4/1999 | Ouchi |
| 5,575,771 A | 11/1996 | Walinsky | | 5,902,310 A | 5/1999 | Foerster et al. |
| 5,584,879 A | 12/1996 | Reimold et al. | | 5,904,697 A | 5/1999 | Gifford, III et al. |
| 5,591,205 A | 1/1997 | Fowler | | 5,906,631 A | 5/1999 | Imran |
| 5,593,412 A | 1/1997 | Martinez et al. | | 5,907,893 A | 6/1999 | Zadno-Azizi et al. |
| 5,601,602 A | 2/1997 | Fowler | | 5,910,155 A | 6/1999 | Ratcliff et al. |
| 5,609,597 A | 3/1997 | Lehrer | | 5,919,207 A | 7/1999 | Taheri |
| 5,613,974 A | 3/1997 | Andreas et al. | | 5,922,009 A | 7/1999 | Epstein et al. |
| 5,618,291 A | 4/1997 | Thompson et al. | | 5,928,231 A | 7/1999 | Klein et al. |
| 5,620,452 A | 4/1997 | Yoon | | 5,928,251 A | 7/1999 | Aranyi et al. |
| 5,620,461 A | 4/1997 | Muijs et al. | | 5,935,147 A | 8/1999 | Kensey et al. |

| Patent No. | Kind | Date | Inventor |
|---|---|---|---|
| 5,938,667 | A | 8/1999 | Peyser et al. |
| 5,941,890 | A | 8/1999 | Voegele et al. |
| 5,947,999 | A | 9/1999 | Groiso |
| 5,951,518 | A | 9/1999 | Licata et al. |
| 5,951,576 | A | 9/1999 | Wakabayashi |
| 5,951,589 | A | 9/1999 | Epstein et al. |
| 5,957,936 | A | 9/1999 | Yoon et al. |
| 5,957,938 | A | 9/1999 | Zhu et al. |
| 5,957,940 | A | 9/1999 | Tanner et al. |
| 5,964,782 | A | 10/1999 | Lafontaine et al. |
| 5,976,161 | A | 11/1999 | Kirsch et al. |
| 5,984,934 | A | 11/1999 | Ashby et al. |
| 5,984,949 | A | 11/1999 | Levin |
| 5,993,468 | A | 11/1999 | Rygaard |
| 5,993,476 | A | 11/1999 | Groiso |
| 6,001,110 | A | 12/1999 | Adams |
| 6,004,341 | A | 12/1999 | Zhu et al. |
| 6,007,563 | A | 12/1999 | Nash et al. |
| 6,010,517 | A | 1/2000 | Baccaro |
| 6,013,084 | A | 1/2000 | Ken et al. |
| 6,015,815 | A | 1/2000 | Mollison |
| 6,019,779 | A | 2/2000 | Thorud et al. |
| 6,022,372 | A | 2/2000 | Kontos |
| 6,024,750 | A | 2/2000 | Mastri |
| 6,030,364 | A | 2/2000 | Durgin et al. |
| 6,030,413 | A | 2/2000 | Lazarus |
| 6,033,427 | A | 3/2000 | Lee |
| 6,036,703 | A | 3/2000 | Evans et al. |
| 6,036,720 | A | 3/2000 | Abrams et al. |
| 6,045,570 | A | 4/2000 | Epstein et al. |
| 6,048,358 | A | 4/2000 | Barak |
| 6,056,768 | A | 5/2000 | Cates et al. |
| 6,056,769 | A | 5/2000 | Epstein et al. |
| 6,056,770 | A | 5/2000 | Epstein et al. |
| 6,059,800 | A | 5/2000 | Hart et al. |
| 6,059,825 | A | 5/2000 | Hobbs et al. |
| 6,063,085 | A | 5/2000 | Tay et al. |
| 6,063,114 | A | 5/2000 | Nash et al. |
| 6,071,300 | A | 6/2000 | Brenneman et al. |
| 6,077,281 | A | 6/2000 | Das |
| 6,077,291 | A | 6/2000 | Das |
| 6,080,182 | A | 6/2000 | Shaw et al. |
| 6,080,183 | A | 6/2000 | Tsugita et al. |
| 6,083,242 | A | 7/2000 | Cook |
| 6,090,130 | A | 7/2000 | Nash et al. |
| 6,102,271 | A | 8/2000 | Longo et al. |
| 6,110,184 | A | 8/2000 | Weadock |
| 6,113,612 | A | 9/2000 | Swanson et al. |
| 6,117,125 | A | 9/2000 | Rothbarth et al. |
| 6,117,148 | A | 9/2000 | Ravo |
| 6,117,157 | A | 9/2000 | Tekulve |
| 6,120,524 | A | 9/2000 | Taheri |
| 6,126,675 | A | 10/2000 | Shchervinsky et al. |
| 6,136,010 | A | 10/2000 | Modesitt et al. |
| 6,146,385 | A | 11/2000 | Torrie et al. |
| 6,149,660 | A | 11/2000 | Laufer et al. |
| 6,149,667 | A | 11/2000 | Hovland et al. |
| 6,152,144 | A | 11/2000 | Lesh et al. |
| 6,152,936 | A | 11/2000 | Christy et al. |
| 6,152,937 | A | 11/2000 | Peterson et al. |
| 6,165,204 | A | 12/2000 | Levinson et al. |
| 6,171,277 | B1 | 1/2001 | Ponzi |
| 6,171,329 | B1 | 1/2001 | Shaw et al. |
| 6,179,849 | B1 | 1/2001 | Yencho et al. |
| 6,193,708 | B1 | 2/2001 | Ken et al. |
| 6,193,734 | B1 | 2/2001 | Bolduc et al. |
| 6,197,042 | B1 | 3/2001 | Ginn et al. |
| 6,198,974 | B1 | 3/2001 | Webster, Jr. |
| 6,200,329 | B1 | 3/2001 | Fung et al. |
| 6,206,895 | B1 | 3/2001 | Levinson |
| 6,206,913 | B1 | 3/2001 | Yencho et al. |
| 6,206,931 | B1 | 3/2001 | Cook et al. |
| 6,210,407 | B1 | 4/2001 | Webster |
| 6,220,248 | B1 | 4/2001 | Voegele et al. |
| 6,221,102 | B1 | 4/2001 | Baker et al. |
| 6,245,079 | B1 | 6/2001 | Nobles et al. |
| 6,248,124 | B1 | 6/2001 | Pedros et al. |
| 6,254,617 | B1 | 7/2001 | Spence et al. |
| 6,254,642 | B1 | 7/2001 | Taylor |
| 6,267,773 | B1 | 7/2001 | Gadberry et al. |
| 6,273,903 | B1 | 8/2001 | Wilk |
| 6,276,704 | B1 | 8/2001 | Suiter |
| 6,277,140 | B2 | 8/2001 | Ginn et al. |
| 6,280,460 | B1 | 8/2001 | Bolduc et al. |
| 6,287,322 | B1 | 9/2001 | Zhu et al. |
| 6,296,657 | B1 | 10/2001 | Brucker |
| 6,302,898 | B1 | 10/2001 | Edwards et al. |
| 6,305,891 | B1 | 10/2001 | Burlingame |
| 6,319,258 | B1 | 11/2001 | McAllen, III et al. |
| 6,322,580 | B1 | 11/2001 | Kanner |
| 6,328,727 | B1 | 12/2001 | Frazier et al. |
| 6,329,386 | B1 | 12/2001 | Mollison |
| 6,334,865 | B1 | 1/2002 | Redmond et al. |
| 6,348,064 | B1 | 2/2002 | Kanner |
| 6,358,258 | B1 | 3/2002 | Arcia et al. |
| 6,375,671 | B1 | 4/2002 | Kobayashi et al. |
| D457,958 | S | 5/2002 | Dycus |
| 6,383,208 | B1 | 5/2002 | Sancoff et al. |
| 6,391,048 | B1 | 5/2002 | Ginn et al. |
| 6,395,015 | B1 | 5/2002 | Borst et al. |
| 6,398,752 | B1 | 6/2002 | Sweezer et al. |
| 6,402,765 | B1 | 6/2002 | Monassevitch et al. |
| 6,409,739 | B1 | 6/2002 | Nobles et al. |
| 6,419,669 | B1 | 7/2002 | Frazier et al. |
| 6,423,054 | B1 | 7/2002 | Ouchi |
| 6,425,911 | B1 | 7/2002 | Akerfeldt et al. |
| 6,428,472 | B1 | 8/2002 | Haas |
| 6,428,548 | B1 | 8/2002 | Durgin et al. |
| 6,443,158 | B1 | 9/2002 | LaFontaine et al. |
| 6,443,963 | B1 | 9/2002 | Baldwin et al. |
| 6,447,540 | B1 | 9/2002 | Fontaine et al. |
| 6,450,391 | B1 | 9/2002 | Kayan et al. |
| 6,458,130 | B1 | 10/2002 | Frazier et al. |
| 6,461,364 | B1 | 10/2002 | Ginn et al. |
| 6,482,224 | B1 | 11/2002 | Michler et al. |
| 6,488,692 | B1 | 12/2002 | Spence et al. |
| 6,500,115 | B2 | 12/2002 | Krattiger et al. |
| 6,506,210 | B1 | 1/2003 | Kanner |
| 6,508,828 | B1 | 1/2003 | Akerfeldt et al. |
| 6,517,569 | B2 | 2/2003 | Mikus et al. |
| 6,533,762 | B2 | 3/2003 | Kanner et al. |
| 6,533,812 | B2 | 3/2003 | Swanson et al. |
| 6,537,288 | B2 | 3/2003 | Vargas et al. |
| 6,547,806 | B1 | 4/2003 | Ding |
| 6,551,319 | B2 | 4/2003 | Lieberman |
| 6,569,173 | B1 | 5/2003 | Blatter et al. |
| 6,569,185 | B2 | 5/2003 | Ungs |
| 6,572,629 | B2 | 6/2003 | Kalloo et al. |
| 6,582,452 | B2 | 6/2003 | Coleman et al. |
| 6,582,482 | B2 | 6/2003 | Gillman et al. |
| 6,596,012 | B2 | 7/2003 | Akerfeldt et al. |
| 6,599,303 | B1 | 7/2003 | Peterson et al. |
| 6,602,263 | B1 | 8/2003 | Swanson et al. |
| 6,610,072 | B1 | 8/2003 | Christy et al. |
| 6,613,059 | B2 | 9/2003 | Schaller et al. |
| 6,616,686 | B2 | 9/2003 | Coleman et al. |
| 6,623,509 | B2 | 9/2003 | Ginn |
| 6,623,510 | B2 | 9/2003 | Carley et al. |
| 6,626,918 | B1 | 9/2003 | Ginn et al. |
| 6,626,920 | B2 | 9/2003 | Whayne |
| 6,632,238 | B2 | 10/2003 | Ginn et al. |
| 6,634,537 | B2 | 10/2003 | Chen |
| 6,645,205 | B2 | 11/2003 | Ginn |
| 6,645,225 | B1 | 11/2003 | Atkinson |
| 6,652,538 | B2 | 11/2003 | Kayan et al. |
| 6,652,556 | B1 | 11/2003 | VanTassel et al. |
| 6,663,655 | B2 * | 12/2003 | Ginn et al. .............. 606/213 |
| 6,669,714 | B2 | 12/2003 | Coleman et al. |
| 6,673,083 | B1 | 1/2004 | Kayan et al. |
| 6,676,671 | B2 | 1/2004 | Robertson et al. |
| 6,676,685 | B2 | 1/2004 | Pedros et al. |
| 6,679,904 | B2 | 1/2004 | Gleeson et al. |
| 6,689,147 | B1 | 2/2004 | Koster, Jr. |
| 6,695,867 | B2 | 2/2004 | Ginn et al. |
| 6,699,256 | B1 | 3/2004 | Logan et al. |
| 6,702,826 | B2 | 3/2004 | Liddicoat et al. |
| 6,712,836 | B1 | 3/2004 | Berg et al. |
| 6,712,837 | B2 | 3/2004 | Akerfeldt et al. |

| | | | | | |
|---|---|---|---|---|---|
| 6,719,777 B2 | 4/2004 | Ginn et al. | 2002/0077657 A1 | 6/2002 | Ginn et al. |
| 6,726,704 B1 | 4/2004 | Loshakove et al. | 2002/0082641 A1 | 6/2002 | Ginn et al. |
| 6,743,195 B2 | 6/2004 | Zucker | 2002/0099389 A1 | 7/2002 | Michler et al. |
| 6,743,243 B1 | 6/2004 | Roy et al. | 2002/0106409 A1 | 8/2002 | Sawhney et al. |
| 6,743,259 B2 | 6/2004 | Ginn | 2002/0107542 A1 | 8/2002 | Kanner et al. |
| 6,749,621 B2 | 6/2004 | Pantages et al. | 2002/0133193 A1 | 9/2002 | Ginn et al. |
| 6,749,622 B2 | 6/2004 | McGuckin et al. | 2002/0151921 A1 | 10/2002 | Kanner et al. |
| 6,755,842 B2 | 6/2004 | Kanner et al. | 2002/0183786 A1 | 12/2002 | Girton |
| 6,767,356 B2 | 7/2004 | Kanner et al. | 2002/0198589 A1 | 12/2002 | Leong |
| 6,776,785 B1 | 8/2004 | Yencho et al. | 2003/0004543 A1 | 1/2003 | Gleeson et al. |
| 6,780,197 B2 | 8/2004 | Roe et al. | 2003/0009180 A1 | 1/2003 | Hinchliffe et al. |
| 6,786,915 B2 | 9/2004 | Akerfeldt et al. | 2003/0032981 A1 | 2/2003 | Kanner et al. |
| 6,790,218 B2 | 9/2004 | Jayaraman | 2003/0045893 A1 | 3/2003 | Ginn |
| 6,790,220 B2 | 9/2004 | Morris et al. | 2003/0055455 A1 | 3/2003 | Yang et al. |
| 6,837,906 B2 | 1/2005 | Ginn | 2003/0065358 A1 | 4/2003 | Frecker et al. |
| 6,846,319 B2 | 1/2005 | Ginn et al. | 2003/0078598 A1 | 4/2003 | Ginn et al. |
| 6,860,895 B1 | 3/2005 | Akerfeldt et al. | 2003/0083679 A1 | 5/2003 | Grudem et al. |
| 6,890,343 B2 | 5/2005 | Ginn et al. | 2003/0093096 A1 | 5/2003 | McGuckin et al. |
| 6,896,687 B2 | 5/2005 | Dakov | 2003/0097140 A1 | 5/2003 | Kanner |
| 6,896,692 B2 | 5/2005 | Ginn et al. | 2003/0109890 A1 | 6/2003 | Kanner et al. |
| 6,926,723 B1 | 8/2005 | Mulhauser et al. | 2003/0125766 A1 | 7/2003 | Ding |
| 6,926,731 B2 | 8/2005 | Coleman et al. | 2003/0144695 A1 | 7/2003 | McGuckin, Jr. et al. |
| 6,929,634 B2 | 8/2005 | Dorros et al. | 2003/0158577 A1 | 8/2003 | Ginn et al. |
| 6,942,674 B2 | 9/2005 | Belef et al. | 2003/0158578 A1 | 8/2003 | Pantages et al. |
| 6,942,691 B1 | 9/2005 | Chuter | 2003/0195504 A1 | 10/2003 | Tallarida et al. |
| 6,964,668 B2 | 11/2005 | Modesitt et al. | 2003/0195561 A1 | 10/2003 | Carley et al. |
| 6,969,397 B2 | 11/2005 | Ginn | 2004/0009205 A1 | 1/2004 | Sawhney |
| 6,989,003 B2 | 1/2006 | Wing et al. | 2004/0009289 A1 | 1/2004 | Carley et al. |
| 6,989,016 B2 | 1/2006 | Tallarida et al. | 2004/0059376 A1 | 3/2004 | Breuniger |
| 7,001,398 B2 | 2/2006 | Carley et al. | 2004/0068273 A1 | 4/2004 | Fariss et al. |
| 7,001,400 B1 | 2/2006 | Modesitt et al. | 2004/0073236 A1 | 4/2004 | Carley et al. |
| 7,008,435 B2 | 3/2006 | Cummins | 2004/0073255 A1 | 4/2004 | Ginn et al. |
| 7,008,439 B1 | 3/2006 | Janzen et al. | 2004/0082906 A1 | 4/2004 | Tallarida et al. |
| 7,033,379 B2 | 4/2006 | Peterson | 2004/0087985 A1 | 5/2004 | Loshakove et al. |
| 7,060,084 B1 | 6/2006 | Loshakove et al. | 2004/0092964 A1 | 5/2004 | Modesitt et al. |
| 7,063,711 B1 | 6/2006 | Loshakove et al. | 2004/0092968 A1 | 5/2004 | Caro et al. |
| 7,083,635 B2 | 8/2006 | Ginn | 2004/0093024 A1 | 5/2004 | Lousararian et al. |
| 7,108,709 B2 | 9/2006 | Cummins | 2004/0093027 A1 | 5/2004 | Fabisiak et al. |
| 7,111,768 B2 | 9/2006 | Cummins et al. | 2004/0097978 A1 | 5/2004 | Modesitt et al. |
| 7,112,225 B2 | 9/2006 | Ginn | 2004/0127940 A1 | 7/2004 | Ginn et al. |
| 7,144,411 B2 | 12/2006 | Ginn et al. | 2004/0143290 A1 | 7/2004 | Brightbill |
| 7,163,551 B2 | 1/2007 | Anthony et al. | 2004/0153122 A1 | 8/2004 | Palermo |
| 7,169,158 B2 | 1/2007 | Sniffin et al. | 2004/0158127 A1 | 8/2004 | Okada |
| 7,169,164 B2 | 1/2007 | Borillo et al. | 2004/0158287 A1 | 8/2004 | Cragg et al. |
| 7,211,101 B2 | 5/2007 | Carley et | 2004/0158309 A1 | 8/2004 | Wachter et al. |
| 7,261,716 B2 * | 8/2007 | Strobel et al. ............... 606/232 | 2004/0167511 A1 | 8/2004 | Buehlmann et al. |
| 7,311,720 B2 | 12/2007 | Mueller et al. | 2004/0167570 A1 | 8/2004 | Pantages et al. |
| 7,316,704 B2 | 1/2008 | Bagaoisan et al. | 2004/0191277 A1 | 9/2004 | Sawhney et al. |
| 7,322,995 B2 | 1/2008 | Buckman et al. | 2004/0215232 A1 | 10/2004 | Belhe et al. |
| 7,326,230 B2 | 2/2008 | Ravikumar | 2004/0249412 A1 | 12/2004 | Snow et al. |
| 7,331,979 B2 | 2/2008 | Khosravi et al. | 2004/0254591 A1 | 12/2004 | Kanner et al. |
| 7,335,220 B2 | 2/2008 | Khosravi et al. | 2004/0267193 A1 | 12/2004 | Bagaoisan et al. |
| D566,272 S | 4/2008 | Walburg et al. | 2004/0267308 A1 | 12/2004 | Bagaoisan et al. |
| 7,361,183 B2 | 4/2008 | Ginn | 2004/0267312 A1 | 12/2004 | Kanner et al. |
| 7,361,185 B2 | 4/2008 | O'Malley et al. | 2005/0038460 A1 | 2/2005 | Jayaraman |
| 7,393,363 B2 | 7/2008 | Ginn | 2005/0038500 A1 | 2/2005 | Boylan et al. |
| 7,396,359 B1 | 7/2008 | Derowe et al. | 2005/0059982 A1 | 3/2005 | Zung et al. |
| 7,431,727 B2 | 10/2008 | Cole et al. | 2005/0075665 A1 | 4/2005 | Brenzel et al. |
| 7,533,790 B1 | 5/2009 | Knodel et al. | 2005/0085851 A1 | 4/2005 | Fiehler et al. |
| 7,597,706 B2 | 10/2009 | Kanner et al. | 2005/0085854 A1 | 4/2005 | Ginn |
| D611,144 S | 3/2010 | Reynolds | 2005/0085855 A1 | 4/2005 | Forsberg |
| 7,806,904 B2 | 10/2010 | Carley et al. | 2005/0090859 A1 | 4/2005 | Ravlkumar |
| 7,819,895 B2 | 10/2010 | Ginn et al. | 2005/0119695 A1 | 6/2005 | Carley et al. |
| 7,841,502 B2 | 11/2010 | Walberg et al. | 2005/0121042 A1 | 6/2005 | Belhe et al. |
| 7,842,068 B2 | 11/2010 | Ginn | 2005/0149117 A1 | 7/2005 | Khosravi et al. |
| 7,850,709 B2 | 12/2010 | Cummins et al. | 2005/0152949 A1 | 7/2005 | Hotchkiss et al. |
| 7,850,797 B2 | 12/2010 | Carley et al. | 2005/0165357 A1 | 7/2005 | McGuckin et al. |
| 7,854,810 B2 | 12/2010 | Carley et al. | 2005/0169974 A1 | 8/2005 | Tenerz et al. |
| 7,857,828 B2 | 12/2010 | Jabba et al. | 2005/0177189 A1 | 8/2005 | Ginn et al. |
| 7,867,249 B2 | 1/2011 | Palermo et al. | 2005/0187564 A1 | 8/2005 | Jayaraman |
| 2001/0007077 A1 | 7/2001 | Ginn et al. | 2005/0216057 A1 | 9/2005 | Coleman et al. |
| 2001/0031972 A1 | 10/2001 | Robertson et al. | 2005/0222614 A1 | 10/2005 | Ginn et al. |
| 2001/0046518 A1 | 11/2001 | Sawhney | 2005/0245876 A1 | 11/2005 | Khosravi et al. |
| 2001/0047180 A1 | 11/2001 | Grudem et al. | 2005/0267528 A1 | 12/2005 | Ginn et al. |
| 2002/0026215 A1 | 2/2002 | Redmond et al. | 2005/0267530 A1 | 12/2005 | Cummins et al. |
| 2002/0038127 A1 | 3/2002 | Blatter et al. | 2005/0273136 A1 | 12/2005 | Belef et al. |
| 2002/0042622 A1 | 4/2002 | Vargas et al. | 2005/0273137 A1 | 12/2005 | Ginn |
| 2002/0049427 A1 | 4/2002 | Wiener et al. | 2005/0274768 A1 | 12/2005 | Cummins et al. |
| 2002/0058960 A1 | 5/2002 | Hudson et al. | 2005/0283188 A1 | 12/2005 | Loshakove et al. |

| | | | | | |
|---|---|---|---|---|---|
| 2006/0030867 A1 | 2/2006 | Zadno | DE | 29723736 U1 | 4/1999 |
| 2006/0034930 A1 | 2/2006 | Khosravi et al. | DE | 19859952 | 2/2000 |
| 2006/0047313 A1 | 3/2006 | Khanna et al. | DE | 102006056283 | 6/2008 |
| 2006/0100664 A1 | 5/2006 | Pai et al. | EP | 0 386 361 | 9/1990 |
| 2006/0167484 A1 | 7/2006 | Carley et al. | EP | 0 534 696 | 3/1993 |
| 2006/0190014 A1 | 8/2006 | Ginn et al. | EP | 0 756 851 | 2/1997 |
| 2006/0190038 A1 | 8/2006 | Carley et al. | EP | 0 774 237 | 5/1997 |
| 2006/0195123 A1 | 8/2006 | Ginn et al. | EP | 0 858 776 | 8/1998 |
| 2006/0195124 A1 | 8/2006 | Ginn et al. | EP | 0 941 697 | 9/1999 |
| 2006/0206146 A1 | 9/2006 | Tenerz | EP | 1 867 287 | 12/2007 |
| 2006/0253037 A1 | 11/2006 | Ginn et al. | FR | 2 443 238 | 7/1980 |
| 2006/0253072 A1 | 11/2006 | Pai et al. | FR | 2 715 290 | 7/1995 |
| 2006/0287674 A1 | 12/2006 | Ginn et al. | FR | 2 722 975 | 2/1996 |
| 2006/0293698 A1 | 12/2006 | Douk | FR | 2 768 324 | 3/1999 |
| 2007/0010853 A1 | 1/2007 | Ginn et al. | GB | 1 358 466 | 7/1974 |
| 2007/0010854 A1 | 1/2007 | Cummins et al. | GB | 2 075 144 | 11/1981 |
| 2007/0021778 A1 | 1/2007 | Carly | GB | 2 397 240 | 7/2004 |
| 2007/0060950 A1 | 3/2007 | Khosravi et al. | IE | S2000/0722 | 10/2001 |
| 2007/0083230 A1 | 4/2007 | Javois | IE | S2000/0724 | 10/2001 |
| 2007/0112304 A1 | 5/2007 | Voss | IE | S2001/0547 | 7/2002 |
| 2007/0112365 A1 | 5/2007 | Hilal et al. | IE | S2001/0815 | 7/2002 |
| 2007/0123817 A1 | 5/2007 | Khosravi et al. | IE | S2001/0748 | 8/2002 |
| 2007/0179527 A1 | 8/2007 | Eskuri et al. | IE | S2001/0749 | 8/2002 |
| 2007/0203507 A1 | 8/2007 | McLaughlin et al. | IE | S2002/0452 | 12/2002 |
| 2007/0225755 A1 | 9/2007 | Preinitz et al. | IE | S2002/0664 | 2/2003 |
| 2007/0225756 A1 | 9/2007 | Preinitz et al. | IE | S2002/0665 | 2/2003 |
| 2007/0225757 A1 | 9/2007 | Preinitz et al. | IE | S2002/0451 | 7/2003 |
| 2007/0225758 A1 | 9/2007 | Preinitz et al. | IE | S2002/0552 | 7/2003 |
| 2007/0239209 A1 | 10/2007 | Fallman | IE | S2003/0424 | 12/2003 |
| 2007/0250080 A1 | 10/2007 | Jones et al. | IE | S2003/0490 | 1/2004 |
| 2007/0265658 A1 | 11/2007 | Nelson et al. | IE | S2004/0368 | 11/2005 |
| 2007/0270904 A1 | 11/2007 | Ginn | IE | S2005/0342 | 11/2005 |
| 2007/0276416 A1 | 11/2007 | Ginn et al. | JP | 58 181006 | 12/1983 |
| 2007/0276488 A1 | 11/2007 | Wachter et al. | JP | 12 74750 | 11/1989 |
| 2007/0282352 A1 | 12/2007 | Carley et al. | JP | 2000102546 | 4/2000 |
| 2008/0004636 A1 | 1/2008 | Walberg et al. | NL | 9302140 | 7/1995 |
| 2008/0004640 A1 | 1/2008 | Ellingwood | PL | 171425 | 4/1997 |
| 2008/0009794 A1 | 1/2008 | Bagaoisan et al. | RU | 2086192 | 8/1997 |
| 2008/0058839 A1 | 3/2008 | Nobles et al. | SU | 495067 | 12/1975 |
| 2008/0065151 A1 | 3/2008 | Ginn | SU | 912155 | 3/1982 |
| 2008/0065152 A1 | 3/2008 | Carley | SU | 1243708 | 7/1986 |
| 2008/0086075 A1 | 4/2008 | Isik et al. | SU | 1324650 | 7/1987 |
| 2008/0093414 A1 | 4/2008 | Bender et al. | SU | 1405828 | 6/1988 |
| 2008/0114395 A1 | 5/2008 | Mathisen et al. | SU | 1456109 | 2/1989 |
| 2008/0210737 A1 | 9/2008 | Ginn et al. | SU | 1560133 | 4/1990 |
| 2008/0221616 A1 | 9/2008 | Ginn et al. | WO | WO 96/24291 | 8/1996 |
| 2008/0243148 A1 | 10/2008 | Mikkaichi et al. | WO | WO 97/07741 | 3/1997 |
| 2008/0269801 A1 | 10/2008 | Coleman et al. | WO | WO 97/20505 | 6/1997 |
| 2008/0269802 A1 | 10/2008 | Coleman et al. | WO | WO 97/27897 | 8/1997 |
| 2008/0272173 A1 | 11/2008 | Coleman et al. | WO | WO 98/06346 | 2/1998 |
| 2008/0300628 A1 | 12/2008 | Ellingwood | WO | WO 98/06448 | 2/1998 |
| 2008/0312666 A1 | 12/2008 | Ellingwood et al. | WO | WO 98/16161 | 4/1998 |
| 2008/0312686 A1 | 12/2008 | Ellingwood | WO | WO 98/17179 | 4/1998 |
| 2008/0312740 A1 | 12/2008 | Wachter et al. | WO | WO 98/18389 | 5/1998 |
| 2008/0319475 A1 | 12/2008 | Clark | WO | WO 98/24374 | 6/1998 |
| 2009/0112306 A1 | 4/2009 | Bonsignore et al. | WO | WO 98/25508 | 6/1998 |
| 2009/0137900 A1 | 5/2009 | Bonner et al. | WO | WO 98/58591 | 12/1998 |
| 2009/0157101 A1 | 6/2009 | Reyes et al. | WO | WO 99/21491 | 5/1999 |
| 2009/0157102 A1 | 6/2009 | Reynolds et al. | WO | WO 99/40849 | 8/1999 |
| 2009/0177212 A1 | 7/2009 | Carley et al. | WO | WO 99/60941 | 12/1999 |
| 2009/0187215 A1 | 7/2009 | Mackiewicz et al. | WO | WO 99/62408 | 12/1999 |
| 2009/0216267 A1 | 8/2009 | Willard et al. | WO | WO 99/62415 | 12/1999 |
| 2009/0230168 A1 | 9/2009 | Coleman et al. | WO | WO 00/06029 | 2/2000 |
| 2009/0287244 A1 | 11/2009 | Kokish | WO | WO 00/07505 | 2/2000 |
| 2010/0114156 A1 | 5/2010 | Mehl | WO | WO 00/07640 | 2/2000 |
| 2010/0114159 A1 | 5/2010 | Roorda et al. | WO | WO 00/27311 | 5/2000 |
| 2010/0168790 A1 | 7/2010 | Clark | WO | WO 00/27313 | 5/2000 |
| 2010/0179567 A1 | 7/2010 | Voss et al. | WO | WO 00/56223 | 9/2000 |
| 2010/0179571 A1 | 7/2010 | Voss | WO | WO 00/56227 | 9/2000 |
| 2010/0179572 A1 | 7/2010 | Voss et al. | WO | WO 00/56228 | 9/2000 |
| 2010/0179589 A1 | 7/2010 | Roorda et al. | WO | WO 00/71032 | 11/2000 |
| 2010/0179590 A1 | 7/2010 | Fortson et al. | WO | WO 01/21058 | 3/2001 |
| 2010/0185234 A1 | 7/2010 | Fortson et al. | WO | WO 01/35832 | 5/2001 |
| 2010/0217132 A1 | 8/2010 | Ellingwood et al. | WO | WO 01/47594 | 7/2001 |
| 2012/0035630 A1 | 2/2012 | Roorda | WO | WO 01/49186 | 7/2001 |
| | | | WO | WO 01/91628 | 12/2001 |
| FOREIGN PATENT DOCUMENTS | | | WO | WO 02/19915 | 3/2002 |
| CA | 2 339 060 | 2/2000 | WO | WO 02/19920 | 3/2002 |
| DE | 197 11 288 | 10/1998 | WO | WO 02/19922 | 3/2002 |

| | | |
|---|---|---|
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/05585 | 1/2007 |
| WO | WO 2007/25014 | 3/2007 |
| WO | WO 2007/81836 | 7/2007 |
| WO | WO 2007/88069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 12/961,331, filed Dec. 6, 2010, Voss.
U.S. Appl. No. 12/966,923, filed Dec. 13, 2010, Cummins et al.
U.S. Appl. No. 12/973,204, filed Dec. 20, 2010, Jabba et al.
U.S. Appl. No. 12/987,792, filed Jan. 10, 2011, Palermo et al.
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-7.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Inlet Medical Inc. Brochure, pp. 1-2, referencing OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht Micabg Workshop 2, The Annals of thoracic surgery, Apr. 1996, pp. S122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive. org, Jun. 1998, Original Publisher: http://prostar.com, may also be found at http://web.archive.org/web/19980630040429/www. perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radio!, Nurnberg, Germany (Reprint).
Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Stretch Comb by Scunci, retrieved via internet at www.scunci.com/productdetail by examiner on Oct. 9, 2007, publication date unavailable.

Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Taber's Cyclopedic Medical Dictionary, 18th Ed. 1997, pp. 797 and 1420.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-22, pp. 2428, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837 Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,895, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Amendment Under 312.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner's Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.

U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/517,004, Nov. 23, 2010, Issue Notification.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/541,083, Dec. 1, 2010, Issue Notification.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/638,115, Dec. 22, 2010, Issue Notification.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/048,503, Dec. 8, 2010, Issue Notification.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/198,811, Oct. 20, 2010, Issue Notification.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/406,203, Oct. 6, 2010, Issue Notification.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.

U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/852,190, Jun. 24, 2010, Office Action.
U.S. Appl. No. 11/852,190, Nov. 1, 2010, Office Action.
U.S. Appl. No. 11/958,281, Sep. 2, 2010, Office Action.
U.S. Appl. No. 11/958,281, Oct. 8, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 11/959,334, Nov. 10, 2010, Issue Notification.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/114,031, Oct. 5, 2010, Office Action.
U.S. Appl. No. 12/114,031, Nov. 22, 2010, Office Action.
U.S. Appl. No. 12/114,091, Oct. 27, 2010, Office Action.
U.S. Appl. No. 12/114,091, Dec. 17, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,256, Nov. 23, 2010, Issue Notification.
U.S. Appl. No. 12/403,277, Jul. 8, 2010, Office Action.
U.S. Appl. No. 12/403,277, Oct. 12, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, filed Nov. 12, 2010, Carley et al.
U.S. Appl. No. 10/006,400, Nov. 10, 2010, Issue Notification.
U.S. Appl. No. 10/435,104, Jan. 12, 2011, Issue Notification.
U.S. Appl. No. 10/667,144, Oct. 28, 2011, Notice of Allowance.
U.S. Appl. No. 11/675,462, Dec. 22, 2011, Notice of Allowance.
U.S. Appl. No. 12/393,877, Dec. 13, 2011, Office Action.
U.S. Appl. No. 12/481,377, Jan. 3, 2012, Office Action.
U.S. Appl. No. 12/548,274, Dec. 28, 2011, Office Action.
U.S. Appl. No. 12/684,470, Dec. 20, 2011, Office Action.
U.S. Appl. No. 12/684,562, Dec. 28, 2011, Office Action.
U.S. Appl. No. 12/684,569, Dec. 20, 2011, Office Action.
U.S. Appl. No. 12/897,358, Jan. 12, 2012, Notice of Allowance.
U.S. Appl. No. 12/941,809, Dec. 13, 2011, Office Action.
U.S. Appl. No. 12/945,646, Oct. 26, 2011, Office Action.
U.S. Appl. No. 12/955,859, Dec. 15, 2011, Office Action.
U.S. Appl. No. 12/402,398, Jan. 24, 2011, Office Action.
U.S. Appl. No. 12/945,646, Jan. 20, 2011, Office Action.
U.S. Appl. No. 12/338,977, Jan. 19, 2012, Office Action.
U.S. Appl. No. 12/684,569, Jan. 27, 2012, Office Action.
U.S. Appl. No. 13/017,636, filed Jan. 31, 2011, Carley et al.
U.S. Appl. No. 10/616,832, Jan. 26, 2011, Issue Notification.
U.S. Appl. No. 11/152,562, Jan. 26, 2011, Issue Notification.
U.S. Appl. No. 13/026,989, filed Feb. 14, 2011, Cummins.
U.S. Appl. No. 10/264,306, Feb. 16, 2011, Issue Notification.
U.S. Appl. No. 11/767,818, Feb. 16, 2011, Office Action.
U.S. Appl. No. 13/030,922, filed Feb. 18, 2011, Cummins.
U.S. Appl. No. 10/356,214, Feb. 23, 2011, Issue Notification.
U.S. Appl. No. 13/039,089, filed Mar. 2, 2011, Palermo et al.
U.S. Appl. No. 11/852,190, Mar. 2, 2011, Office Action.
U.S. Appl. No. 12/122,603, Mar. 3, 2011, Office Action.
U.S. Appl. No. 11/532,576, Mar. 16, 2011, Issue Notification.
U.S. Appl. No. 11/958,281, Mar. 10, 2011, Office Action.
U.S. Appl. No. 11/396,731, Mar. 22, 2011, Office Action.
U.S. Appl. No. 11/427,297, Mar. 21, 2011, Office Action.
U.S. Appl. No. 10/147,774, Apr. 6, 2011, Issue Notification.
U.S. Appl. No. 10/682,459, Apr. 1, 2011, Notice of Allowance.
U.S. Appl. No. 12/403,277, Mar. 31, 2011, Office Action.
U.S. Appl. No. 12/122,603, Apr. 22, 2011, Office Action.
U.S. Appl. No. 12/113,851, Apr. 27, 2011, Office Action.
U.S. Appl. No. 12/481,377, Apr. 28, 2011, Office Action.
U.S. Appl. No. 12/114,031, May 11, 2011, Office Action.
U.S. Appl. No. 12/143,020, May 11, 2011, Office Action.
U.S. Appl. No. 13/112,618, May 20, 2011, Gianotti et al.
U.S. Appl. No. 13/112,631, May 20, 2011, Voss.
U.S. Appl. No. 12/955,859, May 26, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 12/481,377, Jun. 21, 2011, Office Action.
U.S. Appl. No. 12/144,091, Jul. 7, 2011, Office Action.
U.S. Appl. No. 12/945,646, Jul. 6, 2011, Office Action.
U.S. Appl. No. 12/135,858, Jul. 31, 2011, Office Action.
U.S. Appl. No. 12/955,859, Jul. 21, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 10/682,459, Aug. 10, 2011, Issue Notification.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 11/396,731, Sep. 1, 2011, Office Action.
U.S. Appl. No. 13/026,989, Sep. 16, 2011, Office Action.
U.S. Appl. No. 12/122,603, Sep. 23, 2011, Office Action.
U.S. Appl. No. 12/393,877, Sep. 29, 2011, Office Action.
U.S. Appl. No. 60/693,531, filed Jun. 24, 2005, Carly.
U.S. Appl. No. 60/696,069, filed Jul. 1, 2005, Pantages et al.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/097,072, filed Sep. 15, 2008, Sibbitt Jr. et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/481,377, filed Jun. 9, 2009, Clark.

U.S. Appl. No. 12/548,274, filed Aug. 26, 2009, Clark.
U.S. Appl. No. 12/848,642, filed Aug. 2, 2010, Fortson et al.
U.S. Appl. No. 11/767,818, Feb. 3, 2012, Notice of Allowance.
U.S. Appl. No. 12/684,542, Jan. 30, 2012, Restriction Requirement.
U.S. Appl. No. 12/941,809, Jan. 30, 2012, Office Action.
U.S. Appl. No. 12/966,923, Feb. 3, 2012, Notice of Allowance.

U.S. Appl. No. 12/941,809, Jun. 1, 2012, Office Action.
U.S. Appl. No. 12/945,646, May 30, 2012, Issue Notification.
U.S. Appl. No. 13/308,227, filed Nov. 30, 2011, Yribarren.
U.S. Appl. No. 11/744,089, dated Aug. 8, 2012, Office Action.
U.S. Appl. No. 12/955,859, dated Aug. 6, 2012, Office Action.

* cited by examiner

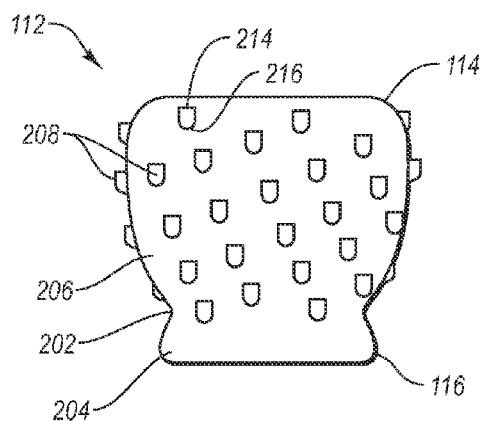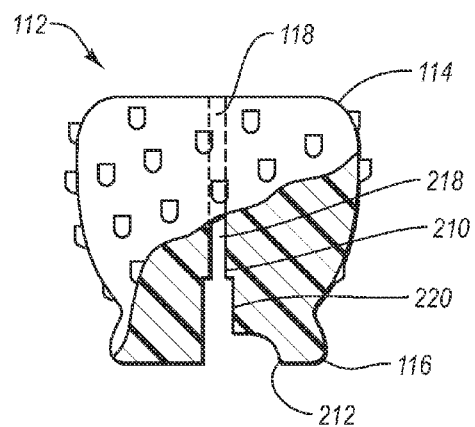
Fig. 2A    Fig. 2B
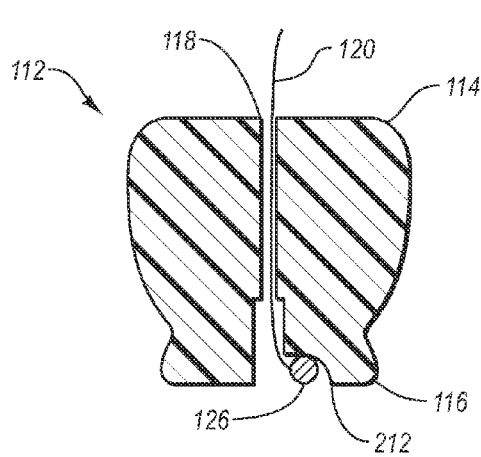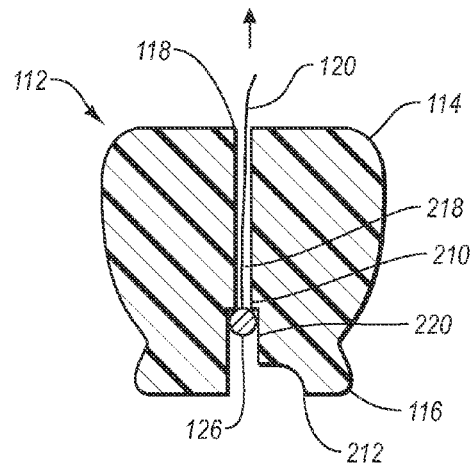
Fig. 2C    Fig. 2D

BIOABSORBABLE PLUG

BACKGROUND

1. The Field of the Invention

The present disclosure relates generally to systems, devices, and methods for the sealing of body lumens. More particularly, the present disclosure relates to techniques for percutaneous closure of arterial and venous puncture sites, which are usually accessed through a tissue tract.

2. Background and Relevant Art

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique. Vascular access is generally provided through an introducer sheath, which is positioned to extend from outside the patient body into the vascular lumen.

When vascular access is no longer required, the introducer sheath is removed and bleeding at the puncture site stopped. One common approach for providing hemostasis (the cessation of bleeding) is to apply external force near and upstream from the puncture site, typically by manual compression. This approach suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, non-optical PTCA results, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may occur, resulting in blood loss through the tract, hematoma and/or pseudo-aneurysm formation, as well as arteriovenous fistula formation. These complications may require blood transfusion and/or surgical intervention.

The incidence of complications from the manual compression procedure increases when the size of the introducer sheath grows larger, and/or when the patient is anticoagulated. The compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable sealing bodies is one example approach that has been proposed. Generally, this example approach relies on the placement of a thrombogenic and bioabsorbable material, such as collagen, at the superficial arterial wall over the puncture site. While potentially effective, this approach suffers from a number of problems. For example, bioabsorbable sealing bodies may lack a solid mechanical attachment of the sealing body to the tissue. Due to the lack of a solid mechanical attachment, the sealing body can wander within the tissue tract or move out of the puncture site, thus causing late bleeds. Conversely, if the sealing body wanders and intrudes too far into the arterial lumen, due to the lack of a solid mechanical attachment, intravascular clots and/or collagen pieces with thrombus attached can form and embolize downstream, causing vascular occlusion.

In addition to not having a solid mechanical attachment to the tissue, the sealing bodies may rely upon expandable materials to achieve hemostasis. Again, the expandable materials lack the security of a hard mechanical closure, thus potentially causing late bleeds and prolonging hemostasis.

Accordingly, devices, systems, and methods that overcome some or all of the disadvantages discussed above would be considered useful.

BRIEF SUMMARY

This Summary is provided to introduce a selection of concepts in a simplified form that are further described below in the Detailed Description. This Summary is not intended to identify key features or essential features of the claimed subject matter.

The present invention provides improved devices, systems, and methods for closing an opening in tissue or a body lumen. The devices, systems, and methods provide a bioabsorbable sealing body that provides a secure mechanical attachment to the tissue. Moreover, implementations of the disclosure may include a mechanical blocking element for achieving hemostasis that is more secure compared to other methods as discussed above.

In one example implementation, a device for closing an opening in tissue includes a proximal end and a distal end. The device further includes a port that extends from the proximal end of the device towards the distal end of the device. In addition to extending from the proximal end of the device towards the distal end of the device, the port includes a restriction zone and a storage region. The device further includes a blocking element that is configured to move between a neutral position, located in the storage region of the port, and a blocking position, located in the restriction zone of the port. When the blocking element is in the blocking position, the blocking element cooperates with the restriction zone in the port to assist in blocking fluid flow through the port.

In another example implementation, a device for closing an opening in tissue includes a proximal end, a distal end, and an outer surface. The configuration of the device is such that a cross-sectional dimension of the device decreases from the proximal end toward the distal end. Moreover, a plurality of projections may extend from at least a portion of the outer surface.

A system for closing an opening in tissue is another example implementation. A system may include an elongate member that has a proximal end, a distal end, and a passage that extends from the proximal end toward the distal end of the elongate member. The system further includes a plug member that is operatively associated with the elongate member. The plug member includes a plug proximal end, a plug distal end, and a port that extends through the plug member from the plug proximal end toward the plug distal end of the plug member. The port is configured to be in operable communication with the passage in the elongate member. The system further includes an actuator that has a proximal end, a distal end, and a blocking element coupled to the distal end of the actuator. The actuator is operatively associated with the passage in the elongate member and the port in the plug member to permit the actuator to move the blocking element between a neutral position and a blocking position within the port. When in the blocking position, the blocking element cooperates with the port to assist in blocking fluid flow through the port.

In another example implementation, a system for closing an opening in tissue includes an elongate member having a proximal end, a distal end, and a passage extending from the proximal end toward the distal end. The system further includes a plug member that is coupled to the elongate member. The plug member includes a plug proximal end, a plug distal end, and an outer surface. A cross-sectional dimension of the plug member decreases from the plug proximal end toward the plug distal end. Furthermore, a plurality of projections may extend from at least a portion of the outer surface.

Yet another example implementation includes a method for closing an opening in a body lumen. The method may include the act of advancing a plug member toward the opening in the body lumen. Additionally, the method may include the act of moving a blocking element from a neutral position to a blocking position within a port in the plug member. When in the blocking position, the blocking element cooperates with the port to assist in blocking fluid flow through the port.

Additional features and advantages of example implementations will be set forth in the description which follows, and in part will be obvious from the description, or may be learned by the practice of the various implementations. The features and advantages may be realized and obtained by means of the instruments and combinations particularly pointed out in the appended claims. These and other features will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 2A illustrates a perspective view of an example device for closing an opening in tissue;

FIG. 2B illustrates a cross-sectional view of an example device for closing an opening in tissue;

FIG. 2C illustrates a cross-sectional view of an example device for closing an opening in tissue with a blocking element in a neutral position;

FIG. 2D illustrates a cross-sectional view of an example device for closing an opening in tissue with a blocking element in a blocking position;

DETAILED DESCRIPTION

The present invention provides improved devices, systems, and methods for closing an opening in a body lumen. The devices, systems, and methods involve a sealing body that may provide a secure mechanical attachment to the tissue. Moreover, implementations of the disclosure may include a mechanical blocking element for achieving hemostasis that is more secure compared to other devices, systems, and methods, as discussed above.

As used herein, the term "distal" is generally defined as in the direction of the patient, or away from a user of a device. In the context of a medical device intervention with or through a vessel wall, "distal" herein refers to the interior or the lumen side of the vessel wall. Conversely, "proximal" generally means away from the patient, or toward the user. In the context of a medical device intervention with or through a vessel wall, "proximal" herein refers to the exterior or outer side of the vessel wall.

Figure 1A:
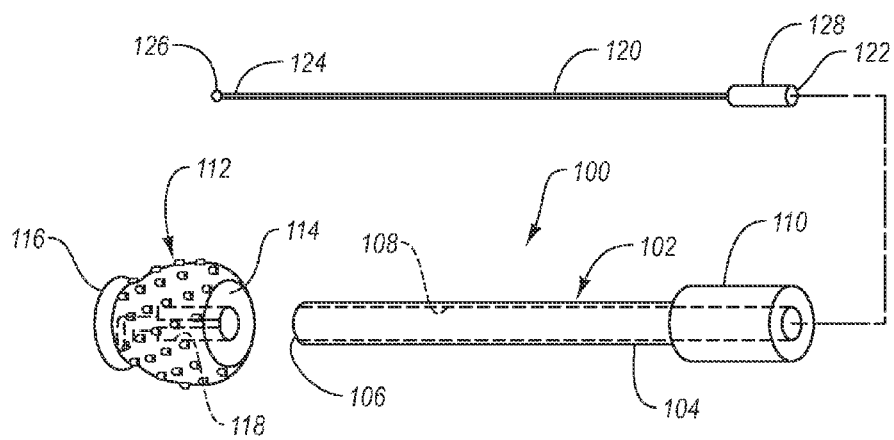
FIG. 1A illustrates an exploded perspective view of an example system for closing an opening in tissue.
Figure 1B:
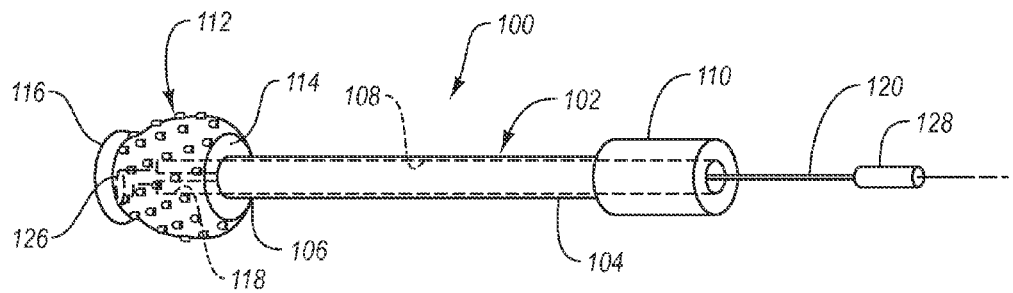
FIG. 1B illustrates an assembled perspective view of an example system for closing an opening in tissue.

Referring now to FIGS. 1A and 1B, a perspective view of an example implementation of a system 100 for closing an opening in tissue is shown. As an overview, the example system 100 includes an elongate member 102 that has a proximal end 104, a distal end 106, and a passage 108 extending from the proximal end 104 to the distal end 106. A handle 110 may be included on the proximal end 104 of the elongate member 102. A plug member 112 is coupled to the distal end 106 of the elongate member 102 and has a proximal end 114, distal end 116, and a port 118 extending from the proximal end 114 to the distal end 116. The port 118 is operatively associated with the passage 108 of the elongate member 102. An actuator 120 extends through the passage 108 and into the port 118 in the plug member 112. The actuator 120 has a proximal end 122, a distal end 124, and a blocking element 126 located at the distal end 124. A pull handle 128 may be provided at the proximal end 122 of the actuator 120.

Systems for closing an opening in tissue, such as system 100, may be implemented in various forms. Accordingly, various configurations of some example implementations will be discussed.

In particular, the geometric configurations of the elongate member 102 may vary from one implementation to the next. For example, the geometric form of the elongate member 102 is one way in which the geometric configuration may vary. As shown in FIGS. 1A and 1B, the elongate member 102 is a tubular member having a generally circular cross-section. In other examples, the elongate member may have an oval cross-section configuration or any other configuration that allows the elongate member to pass through a tissue tract easily.

Just as the configuration of the elongate member 102 may vary, so too may the size of the elongate member vary. The size of the elongate member's cross-section is one way in which the size of the elongate member 102 may vary. In one implementation, shown in FIGS. 1A and 1B, the elongate member 102 has a substantially constant cross-section from the proximal end 104 to the distal end 106. In other implementations, the cross-section of the elongate member 102 may vary (e.g., increase and/or decrease) from the proximal end 104 to the distal end 106. In other implementations, the elongate member 102 may have portions of constant cross-section as well as portions of variable cross-section.

Moreover, the size of the elongate member's cross-section 102 relative to the cross-section of the plug member 112 may also vary. In one example, shown in FIGS. 1A and 1B, the size of the elongate member's cross-section is substantially smaller than the size of the cross-section of the plug member 112, thus minimizing dilation of a tissue tract into which the plug member 112 is inserted. In other implementations, the size of the elongate member's cross-section may be substantially equal to the cross-section of the plug member. In yet other implementations, the size of the elongate member's cross-section may be larger than the cross section of the plug member.

The proximal end 104 of the elongate member 102 may include a handle 110. As illustrated in FIGS. 1A and 1B, the handle 110 is a cylindrical portion provided at the proximal end 104 of the elongate member 102. In other implementations, the handle 110 may be a variety of configurations, including, for example, various shapes and sizes, that facilitate manipulation of the system 100 while in use.

As with the geometric configuration of the elongate member 102, the passage 108 configuration of the elongate member 102 may vary from one implementation to the next. For example, as shown in FIGS. 1A and 1B, the passage 108 has a substantially constant cross-section running from the proximal end 104 to the distal end 106. In other implementations, the passage cross-section may vary (e.g., increase and/or decrease) from the proximal end to the distal end.

In addition to variations in the cross-section, the passage 108 may further include one or more passageways (not shown). The one or more passageways may extend from the passage to the side of the elongate member such that the passageway creates a fluid marker (e.g., blood marker). In this way, a fluid from inside a body lumen, such as blood, is permitted to flow through the passage and out of one or more of the passageways to indicate a particular depth (e.g., when the plug member enters an arterial lumen).

In addition to fluid entering the passage 108, the actuator 120 may be configured to simultaneously extend through the passage 108 in the elongate member 102. Configurations of the actuator 120 may take various forms. For example, the actuator 120 may be formed from a suture material such as a thread of polymeric material that is bioabsorbable (e.g., Vicryl or Monocryl) or natural material (e.g., collagen). Alternatively, the material forming the actuator may be a metal wire. Depending on the type of material used for the actuator, the size of the actuator may also vary. The actuator may be a standard suture size such as 4-0; however, the actuator size may be larger or smaller.

Notwithstanding material or size, the actuator 120 may include a pull handle 128 disposed on the proximal end 122 of the actuator 120, as shown in FIGS. 1A and 1B. The pull handle 128 may take any configuration that permits and/or assists a user in pulling on the actuator 120 in the proximal direction (i.e., away from the patient).

Opposite the pull handle 128, a blocking element 126 is disposed on the distal end 124 of the actuator 120. The blocking element 126 may have various configurations from one implementation to the next. For example, the material of the blocking element 126 may vary. In one implementation, where the actuator is a suture, the blocking element is made from a portion of the suture, such as a knot tied in the distal end of the suture. In other examples, the blocking element may be made from a different material than the suture material or material forming the actuator, such as a bioabsorbable polymer. In any case, the blocking element material 126 may be bioabsorbable, bioresorbable, biodegradable, and/or bioerodible.

Depending on the type of blocking element 126 material, the blocking element 126 may be inflexible such that when the blocking element 126 interfaces with the plug member 112, the plug member 112 material may yield or mold to the blocking element 126 to assist in blocking fluid flow through the port 118. Alternatively, the blocking element 126 material may be flexible such that as the blocking element 126 interfaces with the plug member 112, the blocking element 126 material may yield or mold to the plug member 112 material to assist in blocking fluid flow through the port 118.

The material properties of the blocking element 126 and/or plug member 112 may partially determine the configuration of the blocking element 126, which may vary. FIGS. 1A and 1B show the blocking element 126 having a substantially spherical configuration. In other implementations, the blocking element may take various other configurations, such as a pyramid configuration, an oblong configuration (i.e., an oval, elliptical or otherwise rounded configuration that is not perfectly circular), a random configuration, and any other configuration that is able to interface with the plug member to assist in blocking fluid flow through the port.

In one example implementation, shown in FIG. 1B, the assembled system 100 is configured such that the actuator 120 extends through the passage 108 in the elongate member 102 such that the blocking element 126 is located within and operatively associated with the port 118 of the plug member 112. Furthermore, in the assembled system 100, the pull handle 128 extends from the proximal end 104 of the elongate member 102, also shown in FIG. 1B.

Additionally, the distal end 106 of the elongate member 102 is coupled to the proximal end 114 of the plug member 112. In one example implementation, the plug member 112 and the elongate member 102 may include one or more connectors (not shown) for releasably securing the plug member 112 to the elongate member 102. The one or more connectors may secure the plug member 112 to the elongate member 102 such that the plug member 112 cannot move independently of the elongate member 102. The elongate member 102 may further include an actuator (not shown) that may be activated to release the one or more connectors securing the plug member 112 to the elongate member 102.

Figure 1C:
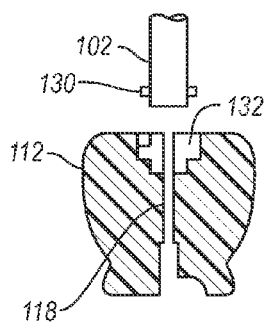
FIG. 1C illustrates a cross-sectional view of an example system for closing an opening in tissue.
Figure 1D:
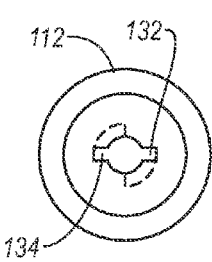
FIG. 1D illustrates a top view of an example device for closing an opening in tissue.
Figure 1E:
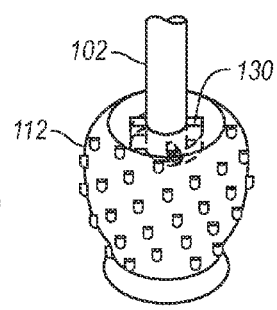
FIG. 1E illustrates a perspective view of an example system for closing an opening in tissue.

In another example implementation, the plug member 112 and the elongate member 102 may be coupled by way of one or more pins 130 on the elongate member 102 that engage one or more slots 132 located within the port 118 of the plug member 112, as illustrated in FIG. 1C-1E. For example, as illustrated in FIG. 1C, the elongate member 102 includes two pins 130 located towards the distal end 106 of the elongate member 102 and are configured to cooperate with the two slots 132 in the plug member 112.

Figure 1F:
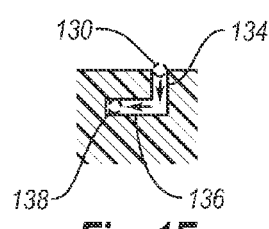
FIG. 1F illustrates a cross-sectional view of an example connection means for an example system for closing an opening in tissue.

In particular, to couple the elongate member 102 to the plug member 112, the pins 132 may enter into a first portion of the slot 134 as shown in FIG. 1D and 1E. The pins 132 are aligned with the first portion of the slot 134 and the elongate member 102 is moved in the distal direction into the port 118 of the plug member 112 until the pins 132 reach a bottom of the first portion 134. FIG. 1F illustrates an enlarged cross-sectional view of an example slot demonstrating the movement of the pin 132 through the first portion of the slot 134. At this point, the elongate member 102 may then be twisted about the axis of the elongate member 102 such that the pins 132 move into a second portion 136 of the slot 132 and into a locked position 138, as shown in FIG. 1F.

When a user wishes to disconnect or decouple the elongate member 102 from the plug member 112, the elongate member 102 may be twisted such that the pins 130 are moved out of the locked position 138 and into the bottom of the first portion 134 of the slot 132. The elongate member 102 may then be moved in the proximal direction and the pins 130 are permitted to exit the slot 132 through the first portion 134.

The configuration of the pins 130 and slots 132 may vary from one implementation to the next. For example, in other implementations there may be more or less than two pins. In one example implementation there may be four pins spaced every ninety degrees around the elongate member 102 with four corresponding slots located in the plug member 112. In another example there may simply be a single pin.

In addition to the number of pins and slots, the configuration of the pins may also vary. FIG. 1C illustrates one example where the pins 130 are generally located at the same distance from the distal end 106 of the elongate member 102. In other implementations, the pins 130 may be offset one from another such that the pins 130 are located at different distances from the distal end 160 of the elongate member 102.

As with the pins 130, the configuration of the slots 132 may also vary from one implementation to the next. As shown in FIGS. 1C through 1F, example slots 132 that have a substantially L-type configuration. In other implementations, the configuration of the slots may take other forms. For example, the first portion 134 of the slot may be on an angle, or curve, relative to the axis of the port 118 such that the slots 132 channel the pins 130 in a manner that forces the elongate member 102 to twist as the pins 130 are moved in or out of the receiving portion.

The interaction of the actuator 120 and the blocking element 126 with the plug member 112 will be discussed in more detail by referencing FIGS. 2A through 2D, which illustrate example implementations of the plug member 112. As with previous aspects of the system 100, the plug member 112 may vary from one implementation to the next. One way in which the plug member 112 may vary is the material of the plug member 112. In one example implementation, the plug member 112 material may be a bioabsorbable, biodegradable, bioerodible, or bioresorbable material such as collagen, polycaprolactone (PCL), poly-D,L-lactic acid, Poly-L-lactic acid, poly(lactide-co-glycolide), poly(hydroxybutyrate), polyanhydrides, and/or poly(glycolic acid) or combinations thereof. In further example implementations, the plug member 112 material may be a material that is not absorbable, erodible or degradable such as a metal or plastic material.

Not only may the plug member 112 material vary, but the plug member 112 configuration may also vary. FIGS. 2A through 2D illustrate one example of the plug member 112 configuration. In this example, the plug member 112 is generally progressively larger from the distal end 116 to the proximal end 114 such that plug member 112 may resist moving in the distal direction (i.e., toward the patient) unless a force is applied to advance the plug member 112 through the tissue tract. In other implementations, the configuration of the plug member 112 may vary and take a variety of configurations that permit the plug member 112 to be advanced through the tissue tract, such as a substantially cylindrical configuration, an oblong configuration, combinations of such, and the like.

The plug member 112 may additionally include one or more features to aid with anchoring the plug member 112 in the tissue tract and/or against the vessel wall. For example, FIG. 2A illustrates a tissue-receiving region 202 that cooperates with an anchor portion 204 located towards the distal end 116 of the plug member 112. In other example implementations, the tissue-receiving region may be located more toward the proximal end of the plug member, thereby creating a larger anchor portion.

The one or more features included in the configuration of the plug member 112 may correlate with the size of the plug member 112. For example, the tissue-receiving region 202 may be sized to be substantially equal to, or slightly larger than, the size of a puncture site in a body lumen, and thus the anchor portion 204 may be sized to be larger than the puncture site in the body lumen. In this way, the configuration of the plug member 112 correlates with the size of the plug member 112 to assist in securing the plug member 112 within the opening in the body lumen.

To further assist with securing the plug member 112 in the opening in the body lumen, FIG. 2A also illustrates an outer surface 206 wherefrom a plurality of projections 208 extend. The configuration of the projections 208 may vary from one implementation to the next, as well as from one projection 208 to the next within the same implementation. As shown in FIG. 2A, the projection 208 has a U-type configuration with a substantially planar top, thereby creating a sharp edge 214 toward the proximal end 114 of the plug member 112, while creating a rounded edge 216 towards the distal end 116 of the plug member 112.

This projection 208 configuration, along with other configurations, permits the advancement of the plug member 112 in the distal direction (i.e., toward the patient) by allowing tissue to glide over the rounded edges 216 of the projections 208. Conversely, the projection 208 configuration resists plug member 112 movement in the proximal direction (i.e., away from the patient) by engaging tissue with the generally planar top that is associated with sharp edges 214 of the projections 208. In other example implementations, the configuration of the projection may be square, round, oblong, triangular, hook-shaped, barb-shaped or any other configuration that permits the plug member 112 to advance in the distal direction while resisting movement in the proximal direction. Moreover, the projections 208 may have various combinations of configurations from one projection 208 to the next on the same plug member 112, such as to aid with optional rotational positioning of the plug member 112 within the tissue tract and vessel.

The degree to which the projections 208 resist movement, or otherwise secure the plug member 112 in place, may depend not only on the configuration but also upon the extent to which the projections 208 extend from the outer surface 206. In one implementation, shown in FIG. 2A, the projections 208 extend about 0.25 mm to about 1.5 mm. In another configuration, the projections 208 extend more or less than the above described range, depending on the size of the puncture. In other examples, the projections may extend from the outer surface to a greater extent such that the length of extension from the outer surface. In still another configuration, the projections extend from the outer surface a perpendicular length equal to about one half the cross-section dimension of the plug member. In further implementations, the length of extension may be shorter or longer. Further, the projections can extend different lengths based upon location of the projection upon the outer surface of the plug member. For instance, the projections may have a shorter extension length near the distal end of the plug member and a larger extension length near the proximal end of the plug member, the length of extension varying gradually or abruptly from the proximal end to the distal end.

Not only may the configuration of the projections 208 vary, but the orientation of the projections 208 may also vary. In FIG. 2A, for example, all the projections 208 have substantially the same orientation with the sharp edge 214 oriented toward the proximal end 114 of the plug member 112. In another example, the orientation of the projections may vary from projection to projection such that the sharp edge of at least a portion of the projections may be positioned to engage the tissue tract when the plug member is moved in a direction other than in the proximal direction (e.g., the projections can resist a rotational movement about the port 118 axis).

The configuration and orientation of the projections 208 may partially determine the arrangement pattern of the projections 208. For example, FIG. 2A illustrates one example arrangement pattern where the projections 208 are arranged in offset columns progressing from the proximal end 114 toward the distal end 116 of the plug member 112. In other implementations, the arrangement pattern of the projections may take various other forms, such as a series of rows, groupings, or completely random patterns.

As with the arrangement pattern, the portion of the outer surface 206 from which the projections 208 extend may vary from one implementation to the next. For example, and as shown in FIG. 2A, the projections 208 generally extend from the proximal end 114 to the tissue-receiving region 202 of the plug member 112. In other implementations, however, the projections may cover substantially the entire outer surface, or alternatively, projections may extend from a small portion of the outer surface.

The number of projections 208 on the outer surface 206 may establish the portion of the outer surface 206 from which the projections 208 extend. For example, FIG. 2A shows one implementation where a substantial plurality of projections 208 extend from the outer surface 206 of the plug member 112. In other implementations, any number of projections may extend from the outer surface and may be fewer or greater than as shown in FIG. 2A.

The material of the projections 208 may also vary. Example projection 208 materials include bioabsorbable, biodegradable, bioerodible, or bioresorbable materials such as collagen, polycaprolactone (PCL), poly-D,L-lactic acid, Poly-L-lactic acid, poly(lactide-co-glycolide), poly(hydroxybutyrate), polyanhydrides, and/or poly(glycolic acid), or combinations thereof. In one implementation, the projection 208 material may be the same material as the plug member 112 material such that the projections 208 absorb, erode, or degrade at substantially the same rate as the plug member 112 material. In another implementation, the projection material may be made of a different material than the plug member material such that the projections absorb, erode, or degrade at a different rate than the plug member material.

Moving from example external configurations of the plug member 112, FIG. 2B illustrates an example of some internal configurations of the plug member 112. In particular, FIG. 2B illustrates an example implementation of the port 118 that extends from the proximal end 114 to the distal end 116. Configurations of the port 118 may vary from one implementation to the next. FIG. 2B illustrates one implementation where the port 118 configuration is substantially cylindrical and includes a first portion 218 and a second portion 220 that are separated by the restriction zone 210; the first portion 218 having a smaller cross-sectional configuration than the second portion 220. In other implementations, the configuration of the port may take various other forms. For example, the port may take a cone configuration such that the cross-sectional dimension of the port progressively increases moving from the proximal end to the distal end of the plug member 112. In yet another implementation, the port 118 may include a cone portion in combination with a cylindrical portion. Various additional port 118 configurations may be used in other example implementations.

In addition to variations in the port 118 configuration, the location of the port 118 within the plug member 112 may also vary. For example, in FIG. 2B the port 118 is substantially aligned along a central axis of the plug member 112. In another example implementation, the port 118 may be located off-center.

Related to the location of the port 118 is the extension path of the port 118 through plug member 112. FIG. 2A, for example, illustrates the port 118 extending along the central axis of the plug member 112 in a straight line that is perpendicular to the proximal end 114 and distal end 116 such that the port 118 directly extends from the proximal end 114 to the distal end 116 of the plug member 112. In other examples, however, the port may extend from the proximal end at an angle relative to the central axis, or the port may curve as it extends through the plug member such that the port extends from the proximal end toward the distal end, but exits the plug member on a side of the plug instead of the distal end.

As with the configuration, location, and extension path of the port 118, the restriction zone 210 located within the port 118 may also vary. For example, the location of the restriction zone 210 may vary from one example implementation to the next. FIG. 2B shows an example implementation where the location of the restriction zone 210 is generally located in the port 118 between the proximal end 114 and the distal end 116 of the plug member 112. However, the location of the restriction zone 210 can be anywhere within the port 118, i.e., the location of the restriction zone can range from the proximal end of the plug member to the distal end of the plug member.

The location of the restriction zone 210 may determine how the restriction zone 210 is formed within the port 118. For example, FIG. 2B shows that the restriction zone 210 may be formed by a step transition between a first portion 218 of the port 118 to a second portion 220 of the port 118, where the first portion 218 has a smaller cross-sectional area than the second portion 220. In other implementations, the restriction zone may be formed by the cross-sectional area of the port progressively decreasing moving from the distal end towards the proximal end such that the cross-sectional dimension of the restriction zone is formed.

As with the restriction zone 210, a storage region 212 of the port 118 may vary. For example, the location of the storage region 212 may vary. FIG. 2B shows one implementation where the storage region 212 is located at the distal end 116 of the plug member 112. In other implementations, the storage region may be located further within the port such that the storage region does not affect the geometry of the distal end of the plug. Moreover, in other implementations, the storage region may be located separate from the port, e.g., the storage region may be located on the distal end of the plug, but may not interact directly with the geometry of the port.

Just as the location of the storage region 212 may vary, so too may the configuration of the storage region 212. FIG. 2B illustrates one example configuration of the storage region 212 that generally has a quarter-circle cross-sectional configuration. However, in various other example implementations, the storage region may have various other cross-sectional configurations, such as a square, rectangular, triangular or any other configuration that would provide a region for storage of the blocking element.

FIG. 2C illustrates an example plug member 112 that depicts an example configuration of the blocking element 126 within the storage region 212 of the port 118. As shown in FIG. 2C, the blocking element 126 and the storage region 212 have a configuration that positions the blocking element 126 in a neutral position within the port 118. In other words, the blocking element 126 is positioned such that an open path exists through the port 118.

The way in which the blocking element 126 is secured in the neutral position within the storage region 212 may vary from one implementation to the next. For example, in the configuration shown in FIG. 2C, the blocking element 126 may be secured in the storage region 212 with a small amount of adhesive (not shown) placed between the blocking element 126 and the storage region 212 wall. The adhesive is configured to secure the blocking element 126 within the storage region 212 until an adequate force is applied to the actuator 120 in the proximal direction to break the adhesive bond between the blocking element 126 and the storage region 212. In another example configuration, the geometry of the storage region 212 may secure the blocking element 126 within the storage region 212. For example, the blocking element 126 may be secured within the storage region 212 by way of a tolerance slip-fit between the blocking element 126 and the storage region 212, wherein the slip-fit tolerance is configured to permit the blocking element 126 to be pulled from the storage region 212 when an adequate force is applied from the actuator 120 in the proximal direction.

After the blocking element 126 is pulled from, or otherwise moved out of the storage region 212, then the blocking element 126 may be positioned in a blocking position as shown in FIG. 2D. For example, as illustrated in FIG. 2D, the blocking element 126 is moved to interact with the restriction zone 210 to assist in blocking fluid flow (e.g., blood) through the port 118.

In other implementations of the invention, the blocking element 126 may cooperate within the first portion 218 of the port 118 rather than the restriction zone 210. In still other configurations, the blocking element may cooperate with other sealing means to assist in blocking fluid flow through the port. For example, an additional sealing means may be formed from a material that expands when exposed to fluids (e.g., a gel foam). Before being exposed to fluid, the sealing means may be in a neutral position within the port; however, upon exposure to fluid (e.g., blood), the sealing element may expand due to hydration or the like.

Figure 3A:
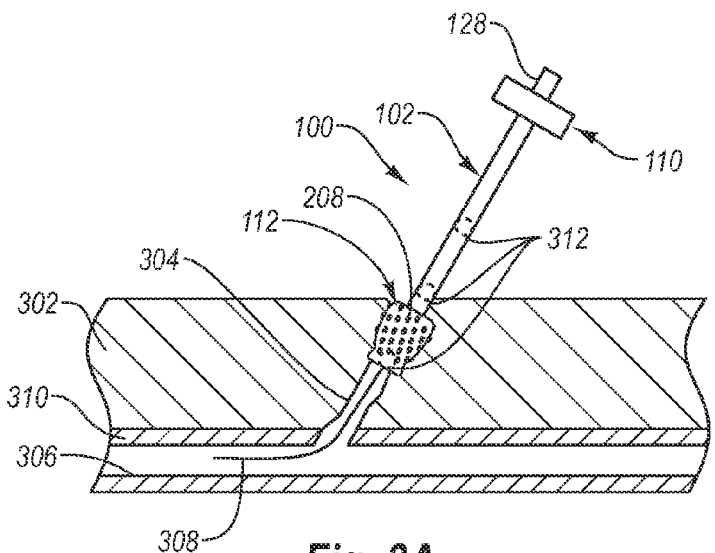
FIG. 3A illustrates a cross-sectional view of an example system for closing an opening in tissue advancing an example device through a tissue tract.
Figure 3B:
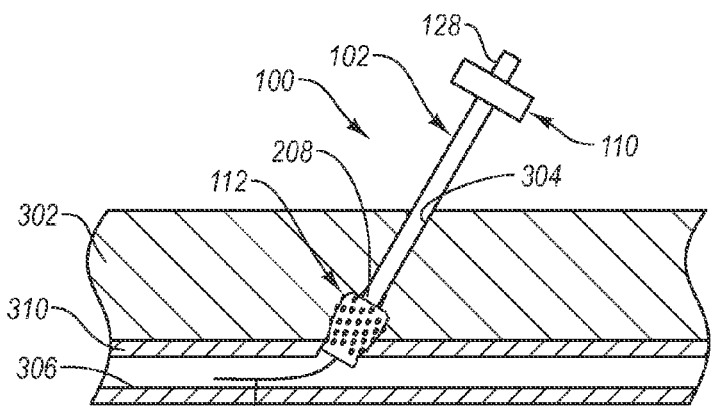
FIG. 3B illustrates a cross-sectional view of an example system for closing an opening in tissue and positioning an example device in a lumen opening.
Figure 3C:
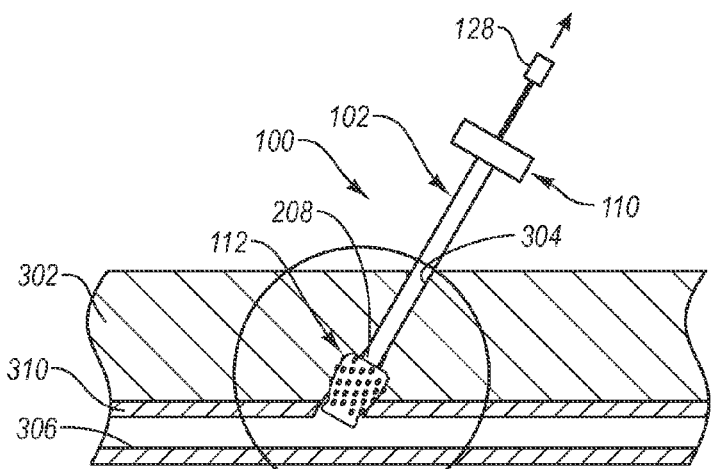
FIG. 3C illustrates a cross-sectional view of an example system for closing an opening in tissue after proper positioning of an example device within a lumen opening is achieved.

Referring now to FIGS. 3A to 3C, during use, the system 100 may assist to seal and/or close a passage through tissue 302, such as a puncture 304 that communicates with a blood vessel 306 or other body lumen. For example, the puncture 304 may have facilitated performance of an endovascular procedure within a patient's vasculature, such as angioplasty, stenting, and atherectomy, or may otherwise provide access via the vessel 306 to a region within the patient's body. Upon completion of the procedure, any instruments, such as an introducer sheath (not shown), may be removed from the vessel 306 and puncture 304. However, a guide wire 308 may be left in the puncture 304 and vessel 306 to assist in guiding the plug member 112 to the proper puncture 304 site in the vessel 306. Alternatively, a guide wire 308 may be introduced to the puncture 304 and vessel 306 after all other instruments are removed.

In one example implementation, a proximal end of the guide wire 308 may be back loaded through the port 118 in the plug member 112 and the passage 108 in the elongate member 102 such that the guide wire 308 may guide the advancement of the plug member 112 in the distal direction (i.e., into the puncture 304 and towards the vessel 306). At this point, the plug member 112 may be introduced into the puncture 304, for example, by initially inserting the distal end 116 of the plug member 112 in the puncture 304, as shown in FIG. 3A. The tapered configuration of the distal end 116 of the plug member 112 may facilitate advancement of the plug member 112 into the puncture 304. Moreover, the configuration of the projections 208 allow the plug member 112 to be advanced towards the vessel 306 with minimal resistance as the tissue 302 is allowed to glide over the projections 208.

The handle 110 located on the proximal end 104 of the elongate member 102 may be used to manipulate and advance the plug member 112 through the puncture 304. As the plug member 112 is progressively advanced further into the puncture 304 and towards the vessel 306, the advancement of the plug member 112 may be monitored. For example, one or more radiopaque markers 312 on the elongate member 102 and/or the plug member 112 may be provided such that the advancement of the plug member 112 through the puncture 304 may be monitored by the use of fluoroscopy. Alternatively, depth markers (not shown) may be provided on the exterior of the elongate member 102 to visually monitor advancement. Tactile indication, e.g., resistance to advancement, may also assist in monitoring the advancement of the plug member 112 into the puncture 304.

As the plug member 112 is advanced, the distal end 116 of the plug member 112 eventually passes though the wall 310 of the vessel 306, as shown in FIG. 3B. One or more of the advancement monitoring techniques described above may confirm that the distal end 116 of the plug member 112 has passed through the wall 310 of the vessel 306. Alternatively, a fluid marker (not shown) within the elongate member 102 may be used to verify that the distal end 116 of the plug member 112 has just passed through the wall 310 of the vessel 306. For example, blood may travel through the port 118 in the plug member 112 and passage 108 in the elongate member 102 and out a fluid marker passageway (not shown) or from the proximal end of the passage 108, such that pulsed blood flow from the fluid marker passageway may indicate that the distal end 116 of the plug member 112 has passed through the wall 310 of the vessel 306.

Once the distal end 116 of the plug member 112 is positioned within the vessel 306, the guide wire 308 may be withdrawn by pulling the guide wire 308 in the proximal direction through the port 118 in the plug member 112 and through the passage 108 in the elongate member 102.

Upon removing the guide wire 308, the port 118 of the plug member 112 is ready to be blocked by the blocking element 126. As shown in FIG. 3C, the pull handle 128 may be moved in the proximal direction, thereby triggering the actuator 120 and causing the blocking element 126 to move from the neutral position within the storage region 212 of the port 118 to a blocking position that may cooperate with the restriction zone 210 of the port 118.

Figure 4A:
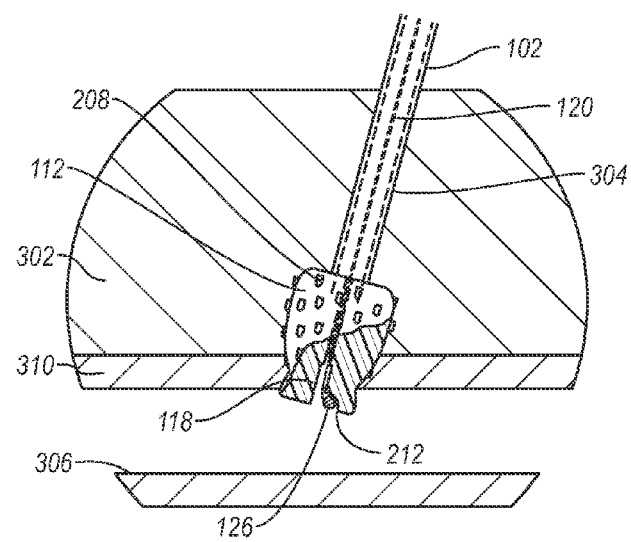
FIG. 4A illustrates a close-up view of an example system for closing an opening in tissue as shown in FIG. 3C.
Figure 4B:
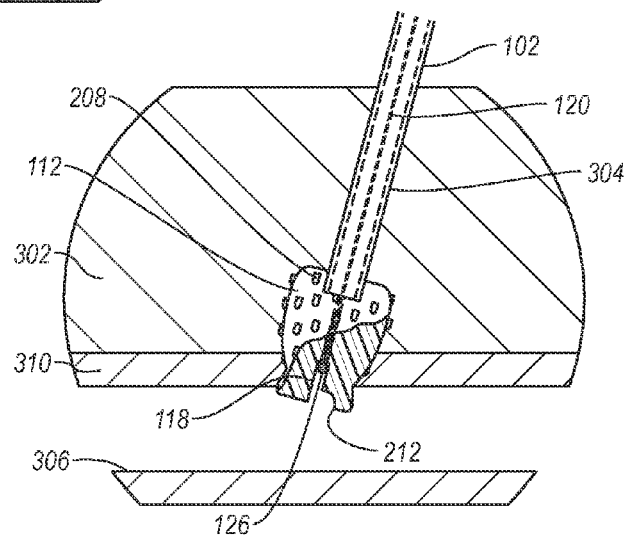
FIG. 4B illustrates a cross-sectional view of an example system for closing an opening in tissue where a blocking element is located in a blocking position.
Figure 4C:
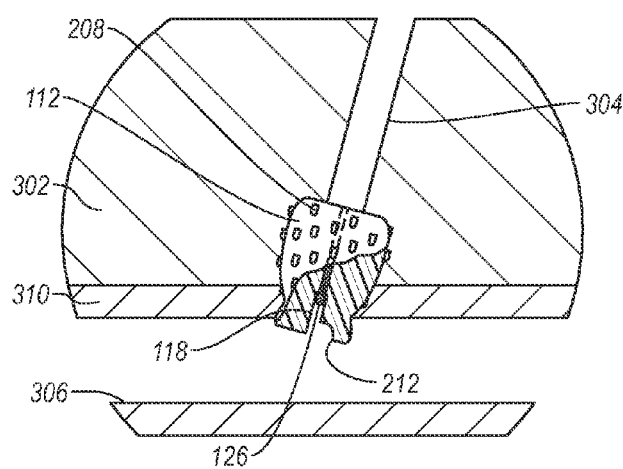
FIG. 4C illustrates a cross-sectional view of an example device for closing an opening in tissue after in an example final position.

In more detail, FIGS. 4A through 4C illustrate the movement of the blocking element 126 from a neutral position in the storage region 212 to a blocking position. In particular, FIG. 4A shows the plug member 112 adequately positioned within the puncture site of the wall 310 of the vessel 306. The guide wire 308 has been withdrawn, thus preparing the port 118 of the plug member 112 to be blocked. The blocking element 126 is positioned within the storage region 212 and connected to the actuator 120.

At this point, shown in FIG. 4B, the actuator 120 is pulled or otherwise withdrawn in the proximal direction such that the blocking element 126 is moved from the neutral position within the storage region 212 to a blocking position within the port 118. In particular, the blocking element 126 may be moved to the restriction zone 210 such that the blocking element 126 cooperates with the geometry of the port 118 to assist in blocking fluid flow through the port 118.

The plug member 112 may then be released from the elongate member 102 and the elongate member 102 withdrawn from the puncture 304 in the tissue 302, as shown in FIG. 4C. The actuator 120 may then be trimmed at the proximal end 114 of the plug member 112, or where the actuator 120 is a suture, the actuator 120 may be used to stitch the puncture 304 in the tissue 302 closed. Alternatively, the actuator 120 may be attached to the blocking element 126 in such away that once the blocking element 126 is secure in the blocking position, the actuator 120 releases from the blocking element 126, and thus the actuator 120 is completely withdrawn from the port 118.

In one example embodiment the plug member 112 may be retained by either a key way locking feature(s) or interference fit feature(s). In particular, key way locking features would essentially be mating slots and bosses that are released by either turning the elongate member 102 or applying forward pressure to the release features. In the case of an interference fit, friction between the geometry of the plug member 112 and the elongate member 102 hold the plug member 112 to the elongate member 102. The interference fit may be released by applying sufficient pressure to the plug member 112 to allow release.

Once the elongate member 102 and the actuator 120 are withdrawn from the puncture 304, the plug member 112 is automatically secured in place. In particular, the tissue-receiving region 202 assists to secure the plug member 112 by permitting the wall 310 of the vessel 306 to engage the geometry of the plug member 112. Furthermore, the projections 208 located on the outer surface 206 of the plug member 112 assist in securing the position of the plug member 112 within the puncture 304 by resisting movement of the plug member 112 in the proximal direction. Finally, the overall configuration of the plug member (e.g., the progressively increasing cross-section dimension of the plug member 112 from the distal end 116 to the proximal end 114) resists movement of the plug member 112 in the distal direction. Thus, the plug member 112 is secured in place to permit hemostasis while the puncture 304 heals.

If the plug member 112 is bioabsorbable, biodegradable, bioerodible or bioresorbable, then the plug member 112 may remain within the puncture 304 as the tissue 302 heals, thereby allowing the wall 310 of the vessel 306 to at least partially heal before the plug member 112 is absorbed.

Figure 5:
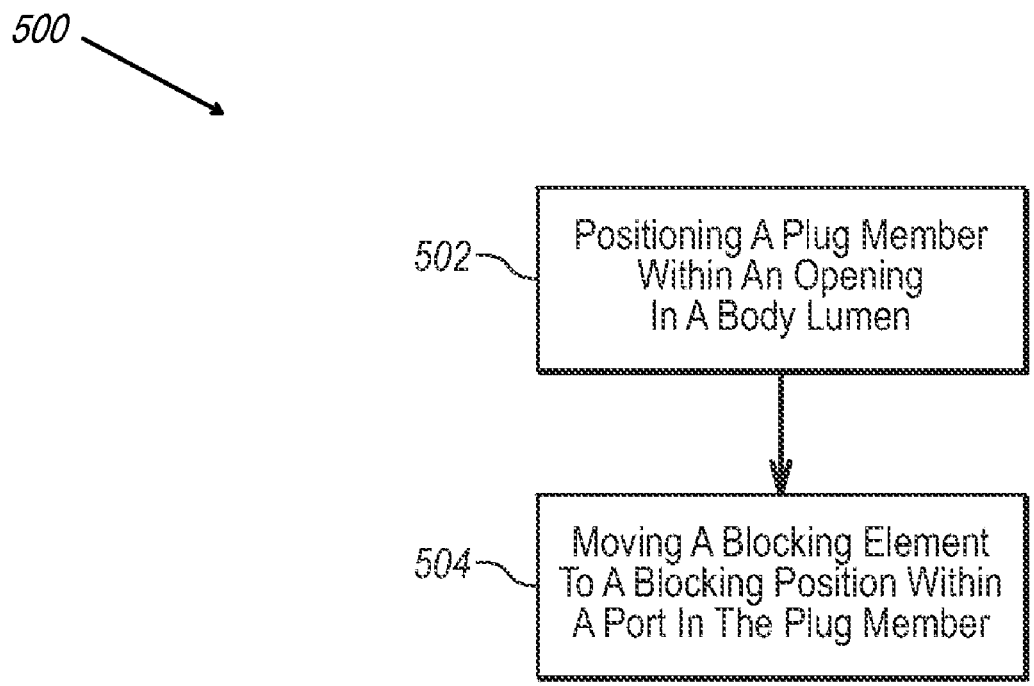
FIG. 5 illustrates an example method for closing an opening in a body lumen.

Accordingly, the previous figures and the corresponding text provide a number of different devices, components and configurations that may be used alone, or in combination, to close an opening in tissue. In addition to the foregoing, implementations of the disclosure can also be described in terms of flowcharts comprising one or more acts in a method for accomplishing a particular result. For example, FIG. 5 illustrates a method 500 of closing an opening in a body lumen. The acts of FIG. 5 are discussed more fully below with respect to the components of FIGS. 1-4.

For example, FIG. 5 shows that a method 500 in accordance with implementations of the disclosure may include positioning a plug member within an opening in a body lumen, as represented by block 502. This may include advancing a plug member toward the opening in the body lumen. For example, and as shown in FIGS. 3A through 3C, a system 100 may be used to advance the plug member 112 within a puncture 304 and to an opening in the wall 310 of the vessel 306.

FIG. 5 also shows that the method 500, in accordance with implementations of the disclosure, may include moving a blocking element to a blocking position within a port in the plug member, as represented by block 504. This may include moving a blocking element from a neutral position to a blocking position within a port in the plug member, wherein the blocking element cooperates with the port to assist in blocking fluid flow through the port when in the blocking position. For example, FIGS. 4A through 4C illustrate the blocking element 126 moving from a neutral position located in the storage region 212 to a blocking position located in a restriction zone 210 by pulling on a actuator 120 in the proximal direction.

Other example implementations may be embodied in other specific forms without departing from the spirit or characteristics contained in this disclosure. The described implementations are to be considered in all respects only as illustrative and not restrictive. The scope of the disclosure is indicated, therefore, by the appended claims rather than by the foregoing description. All changes which come within the meaning and range of equivalency of the claims are to be embraced within their scope.

What is claimed is:

1. A device for closing an opening in tissue, comprising:
a plug member having a proximal end and a distal end;
a port extending from the proximal end towards the distal end; and
a blocking element operatively associated with the port to move between a neutral position and a blocking position, the blocking element having a terminal end and a suture portion extending from the blocking element and having a suture end terminating at the blocking element, the terminal end being within the port in both the neutral position and the blocking position, the neutral position being a position where the blocking element permits fluid flow through the port and the blocking position being a position where the blocking element cooperates with the port to assist in blocking fluid flow through the port.

2. The device as recited in claim 1, the plug member comprising an outer surface with a plurality of projections extending from at least a portion of the outer surface.

3. The device as recited in claim 1, the port comprising:
a storage region for storing the blocking element in the neutral position; and
a restriction zone for receiving the blocking element in the blocking position.

4. The device as recited in claim 1, wherein the blocking element is formed from a knot tied in a suture portion.

5. The device as recited in claim 1, wherein the plug member is made from a bioabsorbable, bioresorbable, biodegradable, or bioerodible material.

6. A device for closing an opening in tissue, the device comprising:
a plug member having a proximal end, a distal end, a port extending through the plug member from the proximal end towards the distal end, and an outer surface extending from the proximal end toward the distal end, a cross-sectional dimension of the plug member decreasing from the proximal end toward the distal end;
a plurality of projections extending from at least a portion of the outer surface; and
a blocking element that cooperates with the port to block fluid flow through the port when moved to a blocking position, the blocking element having a terminal end and a suture portion terminated at and extending from the blocking element, the terminal end being within the port in both a first position that allows fluid to flow through the port and a second position where the terminal end prohibits fluid to flow through the port.

7. The device as recited in claim 6, further comprising a tissue-receiving region located between the proximal end and the distal end of the plug member, the tissue-receiving region having a recess in the outer surface of the plug member.

8. The device as recited in claim 6, wherein the plurality of projections engage the tissue to prevent movement of the plug member.

9. The device as recited in claim 6, wherein the device is made from a bioabsorbable, bioresorbable, biodegradable, or bioerodible material.

10. A system for closing an opening in tissue, comprising:
an elongate member having a proximal end, a distal end, and a passage extending from the proximal end toward the distal end;
a plug member operatively associated with the elongate member, the plug member comprising:
  a plug proximal end and a plug distal end;
  a port extending through the plug member from the plug proximal end towards the plug distal end, the port cooperating with the passage in the elongate member;
a blocking element coupled to a distal end of suture-like actuator, the suture-like actuator operatively associated with the passage in the elongate member and the port in the plug member to permit movement of the blocking element between a neutral position and a blocking position, the blocking element having a terminal end and the suture-like actuator terminated at and extending from the blocking element, the blocking element cooperating with the port to assist in blocking fluid flow through the port when in the blocking position, the terminal end being within the port in both a neutral position that allows fluid to flow through the port and a blocking position where the terminal end prohibits fluid to flow through the port.

11. The system as recited in claim 10, wherein the plug member is releasable from the elongate member.

12. The system as recited in claim 10, the actuator comprising a suture portion and a pull handle on a proximal end of the suture portion.

13. The system as recited in claim 10, wherein the passage in the elongate member further comprises a fluid marker passageway that permits fluid to flow from the port in the plug member through the passage in the elongate member and out the fluid marker passageway.

14. The system as recited in claim 10, wherein the actuator, the blocking element, and the plug member are made from a bioabsorbable, bioresorbable, biodegradable, or bioerodible material.

15. The system as recited in claim 10, the port in the plug member comprising:
a storage region, the blocking element being positioned in the storage region when the blocking element is in the neutral position; and
a restriction zone, the blocking element being positioned in the restriction zone when the blocking element is in the blocking position.

16. The system as recited in claim 15, the restriction zone comprising a transition from a first portion of the port to a second portion of the port,
the second portion of the port having a smaller cross-section dimension than the first portion of the port.

17. The system as recited in claim 10, the elongate member further comprising one or more pins located toward the distal end of the elongate member; and
the plug member further comprising one or more slots that correspond to the one or more pins, the plug member and the elongate member releasably coupled by way of the one or more pins located on the elongate member cooperating with the one or more slots in the plug member.

18. A system for closing an opening in tissue, comprising:
an elongate member having a proximal end, a distal end, and a passage extending from the proximal end toward the distal end;
a plug member coupled to the elongate member, the plug member comprising:
  a plug proximal end, a plug distal end, a port extending from the plug proximal end to the plug distal end, and an outer surface extending from the plug proximal end towards the plug distal end, a cross-sectional dimension of the plug member decreasing from the plug proximal end toward the plug distal end and a diameter of the port increasing in diameter from the plug proximal end toward the plug distal end; a blocking element movable through the port, and a suture terminated at and extending from the blocking element; and
  a plurality of projections extending from at least a portion of the outer surface.

19. The system as recited in claim 18, wherein the elongate member can decouple from the plug member.

20. The system as recited in claim 18, the plug member further comprising a tissue-receiving zone and an anchor portion,
the tissue-receiving zone and the anchor portion being configured to cooperate to interface with a wall in the tissue of a body lumen.

21. A method for closing an opening in a body lumen, the method comprising:
advancing a plug member to the opening in the body lumen, the plug member comprising a proximal end, a distal end, and a port extending from the distal end toward the proximal end; and
moving a blocking element from a neutral position that allows fluid to flow through the port to a blocking position that prohibits fluid to flow through the port, the blocking element having a terminal end and a suture portion terminated at and extending from the blocking element, the terminal end being within the port in both the neutral position and the blocking position, the blocking element and the port cooperating to assist in blocking fluid flow through the port when the blocking element is in the blocking position.

22. The method of claim 21, further comprising:
identifying when a distal end of the plug member is located within the opening in the body lumen.

23. The method of claim 21, wherein moving the blocking element from the neutral position to the blocking position comprises:
pulling a suture portion that is coupled to the blocking element, the blocking element being moved from a storage region within the port to a restriction zone within the port upon pulling the suture portion.

24. The method of claim 21, further comprising slightly withdrawing the plug member;
wherein upon slightly withdrawing the plug member, a plurality of projections, extending from at least a portion of an outer surface of the plug member, engage tissue in a tissue tract.

* * * * *